(12) United States Patent
Asano et al.

(10) Patent No.: US 6,515,089 B1
(45) Date of Patent: *Feb. 4, 2003

(54) TRACE METAL MEASURING METHOD

(75) Inventors: Takaharu Asano, Tsukuba (JP); Hiroshi Nakao, Tsuchiura (JP)

(73) Assignee: Kowa Co., Ltd., Nagoya (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/996,564

(22) Filed: Nov. 30, 2001

(51) Int. Cl.$^7$ ............................................. C08F 126/06
(52) U.S. Cl. ...................... 526/259; 526/263; 526/265; 526/303.1; 526/306; 526/318.2; 526/318.3; 526/321; 526/328.5; 526/333; 526/334; 526/336
(58) Field of Search ................ 526/259, 263, 526/265, 303.1, 306, 318.2, 318.3, 321, 328.5, 333, 334, 336

(56) References Cited

FOREIGN PATENT DOCUMENTS

| | | |
|---|---|---|
| JP | 55-054307 | 4/1980 |
| JP | 7-082285 | 3/1995 |

OTHER PUBLICATIONS

R.F. Pasternack et al., "On the Aggregation of Meso–Substituted Water–Soluble Porphyrins", Journal of the American Chemical Society, 94 (1972), pp. 4511–4517.

E.B. Fleischer et al., "Thermodynamic and Kinetic Properties of an Iron–Porphyrin System", Journal of the American Chemical Society, 93 (1971), pp. 3162–3167.

P. Hambright et al., "The Acid–Base Equilibria, Kinetics of Copper Ion Incorporation, and Acid–Catalyzed Zinc Ion Displacement from the Water–Soluble Porphyrin α, β,γ, δ–Tetra(4–N–methylpyridyl)porphine", Inorganic Chemistry, (1970), vol. 9, No. 7, pp. 1757–1761.

T.P. Stein et al., "The Incorporation of Zinc Ion into a Synthetic Water–Soluble Porphyrin", Journal of the American Chemical Society, 91 (1969), pp. 607–610.

F.R. Longo et al., "The Synthesis and Some Physical Properties of ms–Tetra(pentafluorophenyl)porphin and ms Tetra(pentachlorohenyl)porphin", J. Heterocyclic Chem., (1969), vol. 6, pp. 927–931.

J. Itoh et al., "Spectrophotometric Determination of Copper with α, β, γ, δ–Tetraphenylporphine Trisulfonate", Analytica Chimica Acta, 74 (1975), pp. 53–60.

J. Japan Chemical Soc., 1978, (5), pp. 686–690.

J. Japan Chemical Soc., 1979, (5), pp. 602–606.

Bunseki Kagaku, (1976), vol. 25, pp. 781–784.

*Primary Examiner*—Helen L. Pezzuto
(74) *Attorney, Agent, or Firm*—Oblon, Spivak, McClelland, Maier & Neustadt, P.C.

(57) ABSTRACT

Provided are a method, upon radical copolymerization of a vinyl-containing porphyrin compound and a radically polymerizable monomer, thereby obtaining a porphyrin-nucleus introduced polymer, of controlling reactivity of the porphyrin-nucleus introduced polymer with a metal by selecting the radically polymerizable monomer; and a method for measuring a trace metal by measuring a change in absorbance caused by a complex forming reaction between a porphyrin-nucleus introduced polymer, which has been obtained by radical copolymerization of a vinyl-containing porphyrin compound and a radically polymerizable monomer, and a heavy metal ion, the radically polymerizable monomer being selected so as to heighten reaction selectivity of the porphyrin-nucleus introduced polymer to a metal to be measured. The present invention makes it possible to control the properties or reactivity of the porphyrin-nucleus introduced polymers, which have been obtained from easily available porphyrin compounds without any modification, and by making use of this technique, to provide a highly sensitive method for measuring heavy metals.

16 Claims, 16 Drawing Sheets

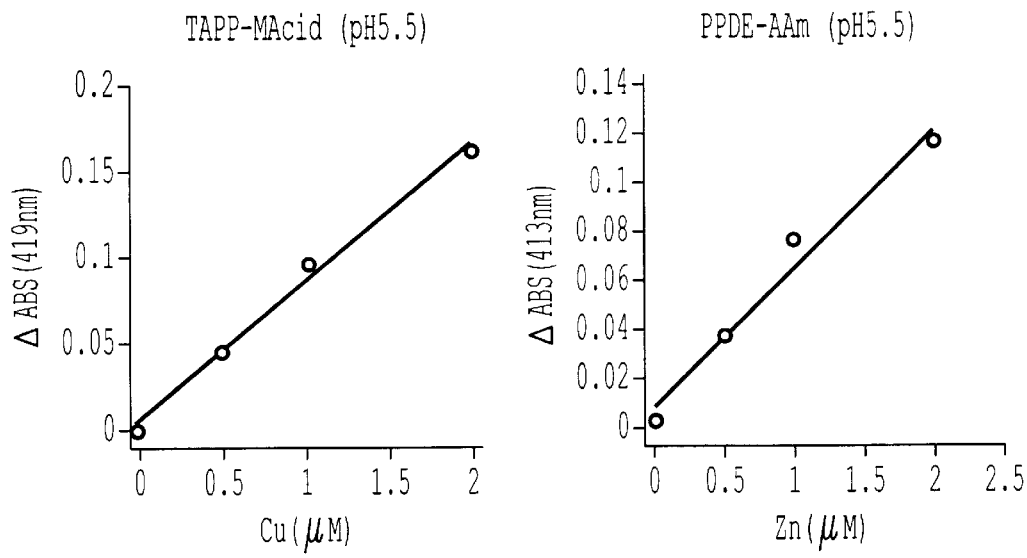
FIG. 5A
FIG. 5B
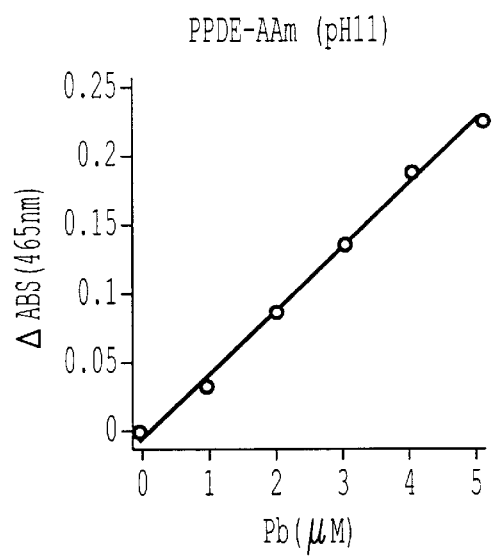
FIG. 5C

TRACE METAL MEASURING METHOD

BACKGROUND OF THE INVENTION

1. Field of the Invention

The present invention relates to a method for measuring the concentration of a trace metal contained in a sample by measuring a change in absorbance caused by a complex forming reaction between a specific porphyrin-nucleus introduced polymer and a metal ion. More specifically, the invention pertains to a method capable of conveniently measuring the concentrations of many heavy metals simultaneously.

2. Discussion of the Background

Heavy metals are classified as "industrial wastes requiring specific management" and are subject to various environmental quality standards. There is a demand for a method of easily measuring the concentration of each of various heavy metals existing in rivers, lakes, marshes, sewage or factory effluent. It is common practice to employ atomic absorption spectrometry or inductively coupled plasma emission spectrometry (ICP) to quantitatively determine the concentration of heavy metals. These methods are not satisfactory for general purposes, because they involve problems such as high cost and the necessity of pipe arrangements or exhaust systems. On the other hand, absorption spectrophotometry does not have a cost problem and permits measurement through a relatively simple apparatus. However, because absorption spectrophotometry can be influenced by many substances that exist in a sample but are not intended to be measured, absorption spectrophotometry often requires a pretreatment of the sample to remove these substances.

Porphyrin compounds are colorimetric reagents used in absorption spectrophotometry. To their porphyrin ring, several metals are bonded, thereby forming complexes. These metals are affected by, as well as external factors such as pH, a substituent or functional group on the molecule of the porphyrin compounds.

As a calorimetric reagent, porphyrin compounds involve problems such as poor solubility in water. For improving their properties including water solubility or reactivity with metals, attempts have been made to substitute the reaction center, and to introduce a substituent or functional group in the vicinity thereof, bringing about great effects. In recent years, synthesis of water soluble porphyrins having various substituents or functional groups have been reported (J. Amer. Chem. Soc., 94 (1972) 4511; J. Amer. Chem. Soc., 93 (1971) 3162; Inorg. Chem., 9(1970)1757: J. Amer. Chem. Soc., 91(1969)607; and J. Heterocycl. Chem., 6(1969)927). There is also a report on the application of these porphyrins to analysis of metals contained at a trace level (ppb level) by making use of a change in fluorescence after formation of a complex with various metals (Analytica Chimica Acta, 74 (1975)53–60; J. Japan Chemical Soc., 1978, (5), 686–690; J. Japan Chemical Soc., 1979, (5), 602–606; BUNSEKI KAGAKU vol. 25 (1976) 781; Japanese patent application laid-open No. 082285/95).

Under the above-described techniques, however, it is necessary to introduce substituents or functional groups to a porphyrin ring in order to impart the porphyrin compound with water solubility or to change reactivity with a metal. An object of the present invention is therefore to develop a technique capable of imparting desired properties or reactivity to easily available porphyrin compounds without any modification, and to provide a highly sensitive method for measuring heavy metals by making use of the technique.

SUMMARY OF THE INVENTION

With the foregoing in view, the present inventors have found that by performing radical copolymerization of a specific porphyrin compound and a radically polymerizable monomer, thereby introducing the porphyrin nucleus into the main chain of the polymer having various side chains and, upon copolymerization, selecting the proper radically polymerizable monomer, it is possible to alter the stereo-structure in the periphery of the porphyrin nucleus without using a porphyrin derivative in which various substituents or functional groups are introduced in the periphery of the porphyrin nucleus and hence to change water solubility of the resulting porphyrin-nucleus introduced polymer or reactivity with a metal upon complex formation. They have also found that highly sensitive and convenient measurement of a target metal can be attained easily by the use of the above-described polymer as a measuring reagent. As a result, they have completed the present invention.

In one aspect of the present invention, there is thus provided a method of, upon radical copolymerization of a vinyl-containing porphyrin compound and a radically polymerizable monomer, selecting the radically polymerizable monomer, thereby controlling the reactivity of the porphyrin-nucleus introduced polymer with a metal.

In another aspect of the present invention, there is also provided a trace metal measuring method by measuring a change in absorbance caused by a complex forming reaction between a porphyrin-nucleus introduced polymer, which has been obtained by radical copolymerization of a vinyl-containing porphyrin compound and a radically polymerizable monomer, and a heavy metal ion, said radically polymerizable monomer being selected so as to heighten reaction selectivity of the porphyrin-nucleus introduced polymer to the target metal.

In the trace metal measuring method according to the present invention, appropriate selection of the radically polymerizable monomer, which is a raw material for the porphyrin-nucleus introduced polymer serving as a measuring reagent, makes it possible to change water solubility of the reagent or reactivity with the metal upon complex formation, thereby facilitating measurement of the target metal with high sensitivity.

BRIEF DESCRIPTION OF THE DRAWINGS

The preferred embodiments of the invention will be described in detail with reference to the following figures.

FIG. 5 illustrates reaction curves of TAPP-MAcid with $Cu^{2+}$ at pH 5.5, PPDE-AAm and $Zn^{2+}$ at pH 5.5 and PPDE-AAm with $Pb^{2+}$ at pH 11.

DETAILED DESCRIPTION OF THE PREFERRED EMBODIMENTS

Figure 1A:
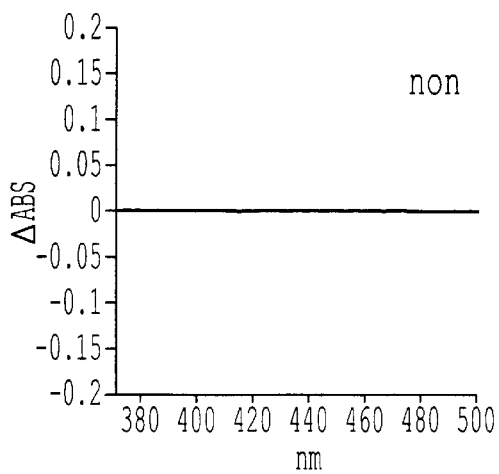
FIG. 1 illustrates a difference in the absorbance caused by the addition of a metal salt to the copolymer of 5,10,15,20-tetrakis {4-(allyloxy)phenyl}-21H,23H-porphyrin (hereinafter abbreviated as "TAPP") and methacrylic acid (hereinafter abbreviated as "MAcid") (pH 5.5).

Although no particular limitation is imposed on the vinyl-containing porphyrin compound to be used in the present invention, those represented by the following formulas (1) to (5) can be employed.

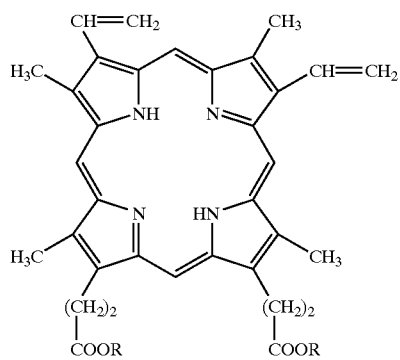

(1)

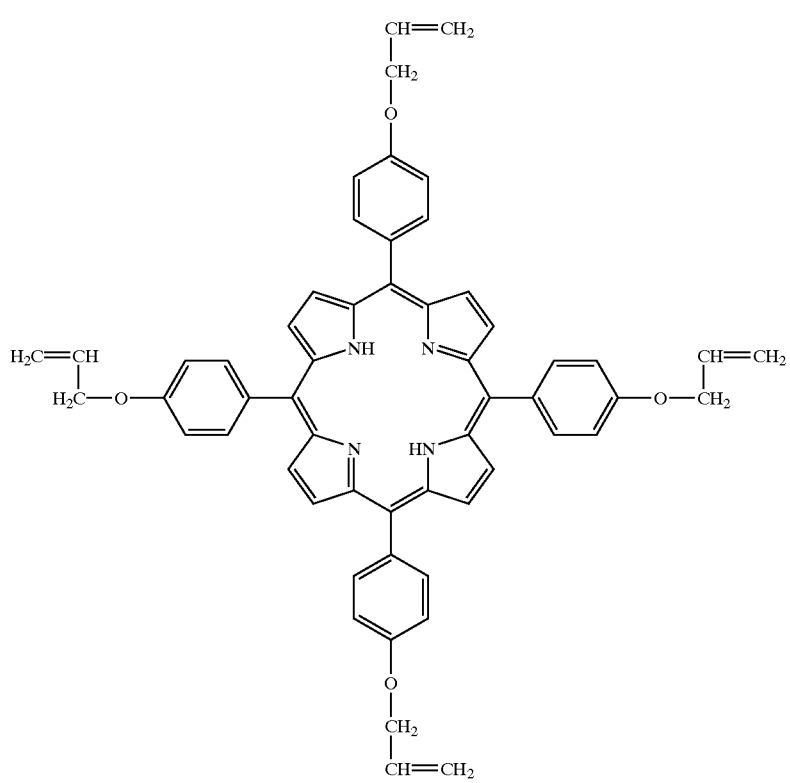

(2)

(3)

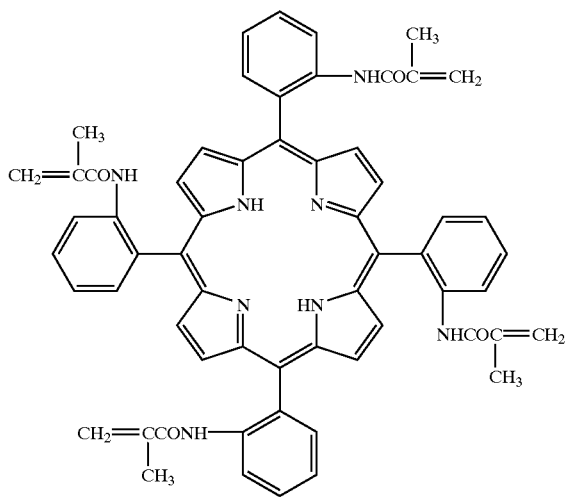

(4)

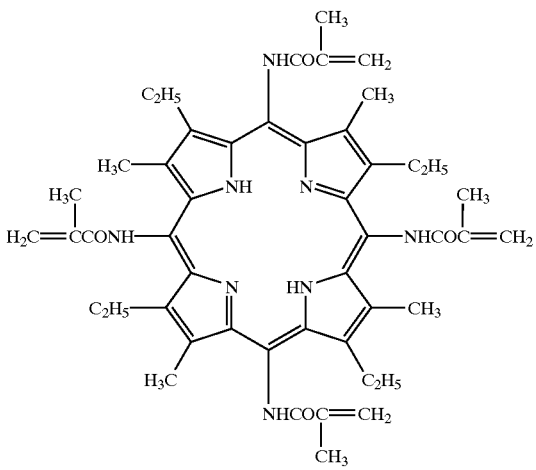

(5)

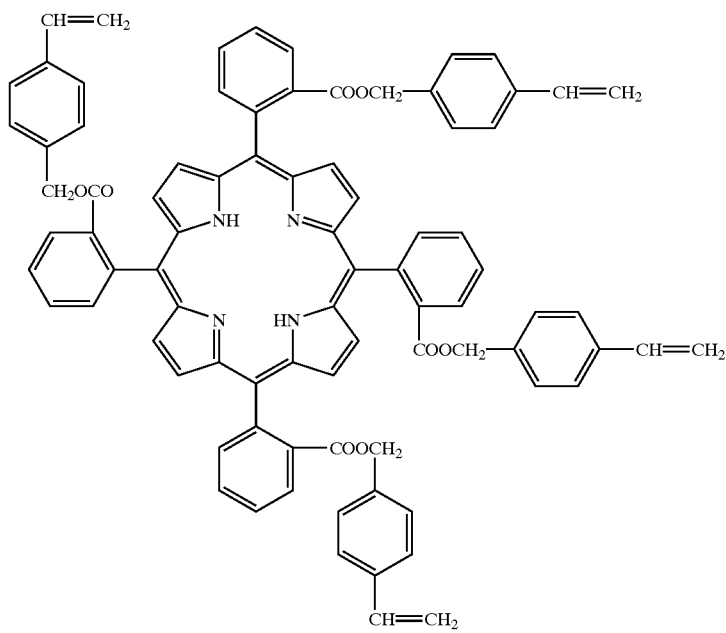

where R represents a hydrogen atom or a $C_{1-6}$ alkyl group. Among them, preferred ones include protoporphyrin IX (hereinafter be abbreviated as "PPfacid") of the formula (1) wherein R represents H, protoporphyrin IX dimethyl ester of the formula (1) wherein R represents a methyl group, and 5,10,15,20-tetrakis {4-(allyloxy)phenyl}-21H,23H-porphyrin of the formula (2). These porphyrin compounds are available commercially or can be synthesized by converting the functional group of the commercially available product.

Although no particular limitation is imposed on the radically polymerizable monomer to be used in the present invention, usable are, for example, compounds represented by the following formula (6):

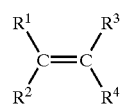

(6)

where $R^1$, $R^2$, $R^3$ and $R^4$ each independently represents a hydrogen atom; a $C_{1-5}$ alkyl group; —$(CH_2)_n COOR^5$, —$(CH_2)_n OCOR^5$, —$(CH_2)_n N(R^5)(R^6)$, —$(CH_2)_n CON(R^5)$ $(R^6)$, or —$(CH_2)_n A$ in which $R^5$ and $R^6$ each represents a hydrogen atom, a $C_{1-5}$ alkyl group, a carboxymethyl group, or a phenyl or phenylalkyl group which may have a substituent, A represents a halogen atom, a hydroxyl group, a formyl group, a cyano group or a carbonyl halide group and n stands for an integer of 0 to 6; or an imidazolyl, pyridyl or phenyl group which may have a substituent.

Specific examples include acrylamide, methacrylic acid, acrylic acid, 5-hexenoic acid, allylamine, 3-butenoic acid, β-methallyl alcohol, allyl alcohol, N,N-dimethylacrylamide, 1-vinylimidazole, 2-vinylpyridine, 4-vinylpyridine, allyl chloride, vinyl acetate, maleamide, maleic acid, dimethyl maleate, diethyl maleate, maleinamic acid, methyl hydrogen maleate, ethyl hydrogen maleate, fumaramide, fumaric acid, dimethyl fumarate, diethyl fumarate, ethyl hydrogen fumarate, fumaronitrile, fumaryl chloride, crotonamide, crotonic acid, crotonaldehyde, methyl crotonate, ethyl crotonate, crotononitrile, crotonoyl bromide, crotonoyl chloride, crotyl alcohol, crotyl bromide, crotyl chloride, isocrotonic acid, trans-1,2-dichloroethylene, citraconic acid, dimethyl citraconate, mesaconic acid, angelic acid, methyl angelate, tiglic acid, methyl tiglate, ethyl tiglate, tigloyl chloride, tiglic aldehyde, N-tigloylglycine, cinnamaldehyde, cinnamamide, cinnamic acid, ethyl cinnamate, methyl cinnamate, cinnamonitrile, cinnamoyl chloride, cinnamyl bromide, cinnamyl chloride, 3-methyl-2-butenal, 2-methyl-2-butene, 2-methyl-2-butenenitrile, 3-methyl-2-buten-1-ol, and cis-1,2-dichloroethylene.

By using, as the radically polymerizable monomer, the above-described compound having one polymerizable carbon-carbon double bond and a compound having at least two polymerizable carbon-carbon double bonds and serving as a crosslinking agent in combination, polymers having various performances such as a polymer gel which has grown three-dimensionally are available. As such a radically polymerizable monomer having at least two polymerizable carbon-carbon double bonds, compounds can be given as examples represented by the following formula (7):

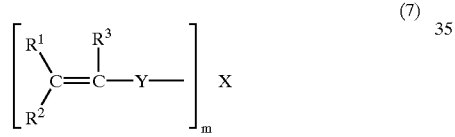

(7)

where $R^1$, $R^2$ and $R^3$ have the same meanings as described above, Y represents a single bond, —(CH$_2$)$_n$COO—, —(CH$_2$)$_n$OCO—, —(CH$_2$)$_n$NR$^5$—, —(CH$_2$)$_n$CONR$^5$—, —(CH$_2$)$_n$O— or —(CH$_2$)$_n$CO— (in which $R^5$ and n have the same meanings as described above), X represents —(CH$_2$)$_n$—, —(CH$_2$)$_n$S—S(CH$_2$)$_n$—, {—(CH$_2$)$_n$—}$_3$CR$^5$, {—(CH$_2$)$_n$—}$_4$C, —φ— or —φ< (in which $R^5$ and same meanings as described above, and φ represents a benzene ring), and m stands for an integer of 2 to 4. Specific examples of such a crosslinking agent include the following compounds.

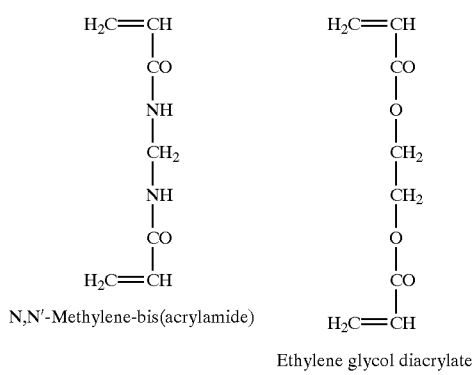

N,N'-Methylene-bis(acrylamide)

Ethylene glycol diacrylate

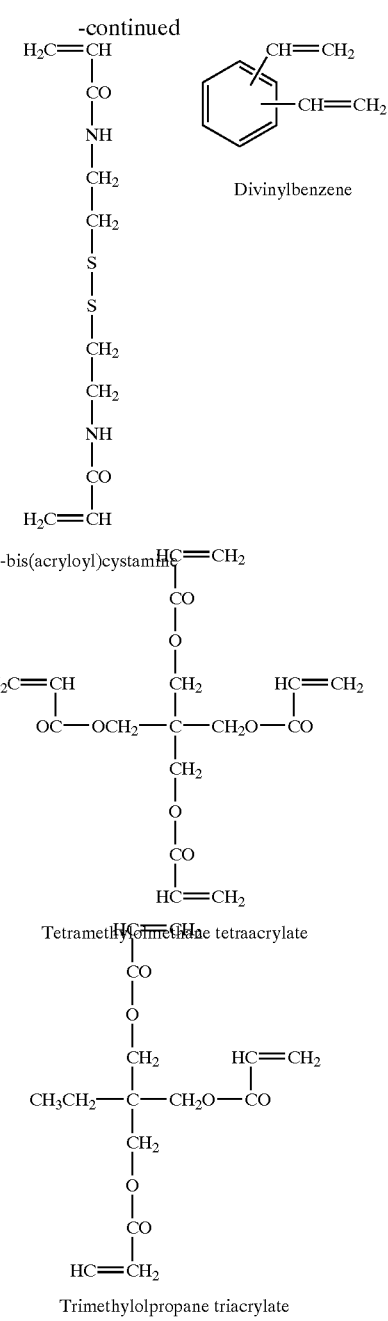

N,N'-bis(acryloyl)cystamine

Tetramethylolmethane tetraacrylate

Divinylbenzene

Trimethylolpropane triacrylate

A weight ratio of the porphyrin compound to the radically polymerizable monomer in the present invention preferably ranges from 1:100 to 1:10,000, with 1:200 to 1:1,000 being especially preferred.

There is no particular limitation imposed on the molecular weight of the porphyrin-nucleus introduced polymer obtained by radical copolymerization of a porphyrin compound and a radically polymerizable monomer. If it is used as a measuring reagent, the resulting polymer preferably has a weight average molecular weight, as measured by the light scattering method, ranging from 50,000 to 5,000,000, with 100,000 to 1,000,000 being especially preferred.

The radical copolymerization of the porphyrin compound and radically polymerizable monomer are conducted in an organic solvent in the presence of a polymerization initiator. Examples of the organic solvent include dimethylsulfoxide (DMSO), tetrahydrofuran (TBF), benzene, chloroform and dimethylformamide (DMF). In particular, DMSO is suited when PPfacid or PPDE is used as the porphyrin compound, while THF is suited when TAPP is used. As the polymerization initiator, azobisisobutyronitrile (AIBN) and 2,2'-azobis (4-methoxy-2,4-dimethylvaleronitrile) can be given as examples.

The reaction is preferably carried out for 5 to 30 hours, especially 15 to 25 hours at 30 to 80° C., especially 55 to 65° C. After reaction, the reaction mixture may be dialyzed for isolation and washing.

The porphyrin-nucleus introduced polymers of the present invention thus obtained differ in reactivity with a metal, depending on the kind of the radically polymerizable monomer used upon radical copolymerization. When the porphyrin-nucleus introduced polymers of the invention are used as a trace metal measuring reagent, highly sensitive and convenient measurement can be attained by using a polymer having high selectivity to a metal to be measured and measuring a change in absorbance caused by complex formation with a heavy metal ion. Use in combination of two or more polymers different in reaction selectivity to metals enables simultaneous measurement of plural metals. When a compound having at least two polymerizable carbon-carbon double bonds is used as the radically polymerizable monomer as described above, the mixture grows three dimensionally into a polymer (gel) which can be easily transformed in various forms such as sheet, film, tube, beads and paste, making it possible to adapt it to a variety of measuring conditions.

A trace metal in a sample can be measured, for example, by adding a porphyrin-nucleus introduced polymer to a buffer solution, measuring absorbance of the resulting mixture by a spectrophotometer, adding the sample containing the trace metal, measuring absorbance again after a lapse of a predetermined time and deriving a metal concentration based on the regression equation built by multiple regression analysis using the value of a standard sample.

When the porphyrin-nucleus introduced polymers of the invention are used as a trace metal measuring reagent, examples of the heavy metal ion to be measured include $Ca^{2+}$, $Cd^{2+}$, $Co^{2+}$, $Cr^{3+}$, $Cu^{2+}$, $Fe^{3+}$, $Fe^{2+}$, $Mg^{2+}$, $Mn^{2+}$, $Ni^{2+}$, $Zn^{2+}$ and $Pb^{2+}$. This reagent is applicable to measurement of any samples taken from rivers, lakes, marshes, sewage, factory effluent, leachate from waste incinerators and the like which need control by environmental quality standards.

EXAMPLES

The present invention will hereinafter be described in further detail by the following examples. It should however be borne in mind that the present invention is not limited to or by them.

Example 1

Synthesis of a Porphyrin-nucleus Introduced Polymer

As the porphyrin compound, PPfacid, PPDE and TAPP were employed, while as the radically polymerizable monomer, the below-described 13 compounds were employed among the above-exemplified ones (the abbreviation in parentheses will hereinafter be used).

Acrylamide (AAm)
Acrylic acid (AAcid)
Allylamine (AAmine)
β-Methallyl alcohol (βMAl)
N,N-dimethylacrylamide (DMAAm)
Methacrylic acid (MAcid)
5-Hexenoic acid (5HAcid)
3-Butenoic acid (3BAcid)
Allyl alcohol (AAl)
1-vinylimidazole (1VImida)
4-Vinylpyridine (4VPyr)
Vinyl acetate (VAce)
Allyl chloride (AChlo)

In a vessel, 10 ml of a 0.6 mM porphyrin solution, an adequate amount of a radically polymerizable monomer and 0.4 ml of 500 mM AIBN were charged, followed by the addition of an organic solvent to give the total amount of 20 ml. The radically polymerizable monomer was added so that the concentration after filling would become 1M. As the solvent, DMSO was used for the synthesis of a PPfacid- or PPDE-introduced polymer, while THF was used for the synthesis of a TAPP-introduced polymer.

The vessel having the reaction mixture therein was immersed in cold water filled in an ultrasonic apparatus, followed by degassing for 30 minutes. Right after bubbling by a nitrogen gas for 2 minutes, the vessel was hermetically sealed. It was placed in an incubator of 60° C. and polymerization was initiated. After 21 hours, the polymer solution was encapsulated in a dialysis membrane (molecular cutoff: 12000 to 14000) for isolation and washing of the polymer and dialyzed against miliQ water in a room at low temperature (4° C.). The polymer insoluble in water precipitated or produced turbidity so that it was dissolved in methanol. In the end, the insoluble matter was removed by filtration through a 0.2 μm filter, whereby solutions of various porphyrin-nucleus introduced polymers were prepared.

Table 1 shows the results of infrared spectroscopic analysis, melting-point measurement and molecular-weight measurement (weight-average molecular weight as measured by light scattering method) of each of the porphyrin-nucleus introduced polymers thus prepared.

TABLE 1

| Polymer | Average molecular weight | IR absorption peak (cm$^{-1}$) | Attributable atomic group | mp (° C.) |
|---|---|---|---|---|
| PPDE-AAm | 276100 | 1655 | —CONH$_2$ | 249–279 |
| PPDE-MAcid | 290700 | 1701 1261 | —COOH | 240–261 |
| PPDE-AAcid | | 1720 1248 | —COOH | — |
| PPDE-1VImida | | | | |
| PPDE-4VPyr | | 1601 1420 824 | pyridine ring | 168–255 |
| PPDE-5HAcid | | | | |
| PPDE-3BAcid | | | | |
| PPDE-VAce | | 1736 1240 | —CO—O— | 78–126 |
| PPDE-AAmine | | | | |
| PPDE-AChlo | | 689 | C—Cl | |
| PPDE-AAl | | 1067 | C—O stretching vibration | |
| PPDE-βMAl | | 1055 | C—O stretching vibration | |
| PPDE-DMAAm | | 1624 | —CO—N tertiary amine | |
| PPfacid-AAm | | 1655 | —CONH$_2$ | |
| TAPP-AAm | | 1655 | —CONH$_2$ | 198–246 |
| TAPP-MAcid | 563700 | 1701 1263 | —COOH | 239–244 |
| TAPP-AAcid | | 1720 1244 | —COOH | — |

TABLE 1-continued

| Polymer | Average molecular weight | IR absorption peak (cm$^{-1}$) | Attributable atomic group | mp (° C.) |
|---|---|---|---|---|
| TAPP-DMAAm | | 1618 | —CO—N tertiary amide | |

Example 2

Measurement of Reactivity with Metal (1) Measuring Method

To 200 μl of a buffer solution, the porphyrin introduced polymer solution and a diluent were added to give the total amount of 1 ml. As the buffer solution, 100 mM 2-(N-morpholino) ethanesulfonic acid (MES) of pH 5.5 and 100 mM 3-cyclohexylamnino-1-propanesulfonic acid (CAPS) of pH 11 were employed, respectively. As the diluent, miliQ water was used for a water soluble polymer, while methanol was used for another polymer. A ratio of the diluent to the polymer solution was adjusted so that the maximum absorbance would become about 1.

By a spectrophotometer, absorbance at 370 to 500 nm was measured with miliQ water or methanol as a blank. Then, 10 μl of a 200 μM aqueous metal salt solution as shown in Table 2 was added. After 15 minutes at 80° C., absorbance was measured again in a similar manner. At this time, a volumetric change due to addition of the metal was considered to be negligible.

TABLE 2

| METAL SALT | METAL ION |
|---|---|
| Calcium chloride | $Ca^{2+}$ |
| Cadmium chloride | $Cd^{2+}$ |
| Cobalt chloride | $Co^{2+}$ |
| Chromium (III) chloride | $Cr^{3+}$ |
| Copper sulfate | $Cu^{2+}$ |
| Iron (III) chloride | $Fe^{3+}$ |
| Iron (II) chloride | $Fe^{2+}$ |
| Magnesium chloride | $Mg^{2+}$ |
| Manganese chloride | $Mn^{2+}$ |
| Nickel chloride | $Ni^{2+}$ |
| Zinc sulfate | $Zn^{2+}$ |
| Lead nitrate | $Pb^{2+}$ |

Figure 1B:
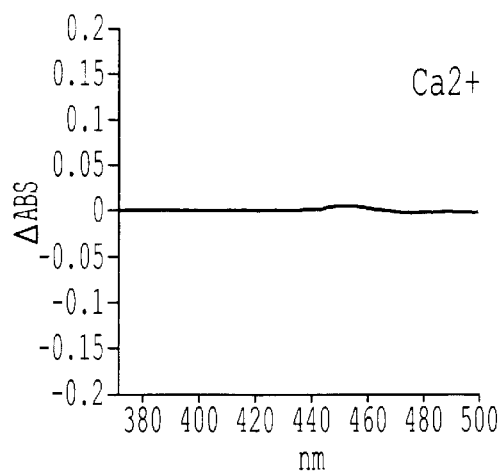
Figure 1C:
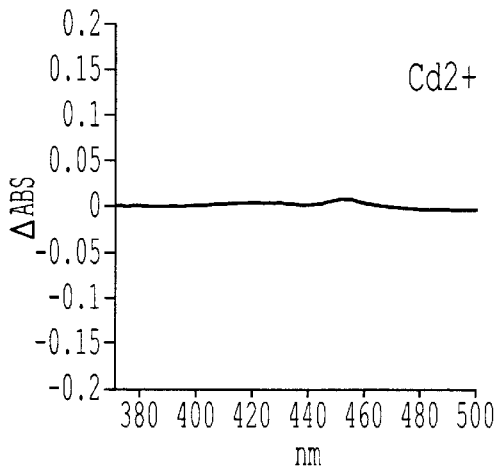
Figure 1D:
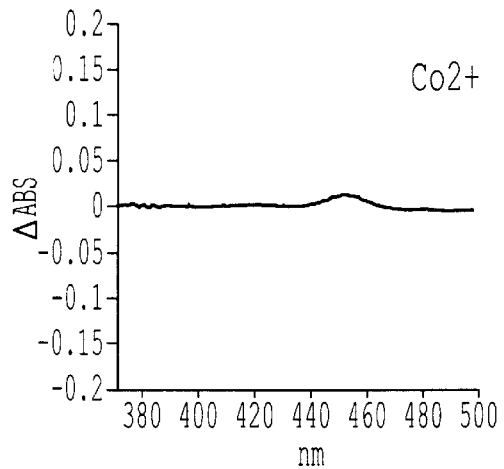
Figure 1E:
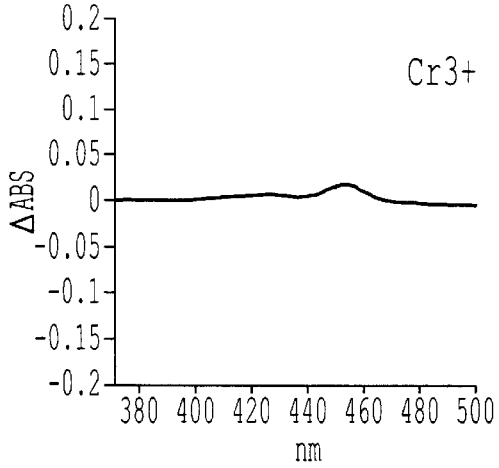
Figure 1F:
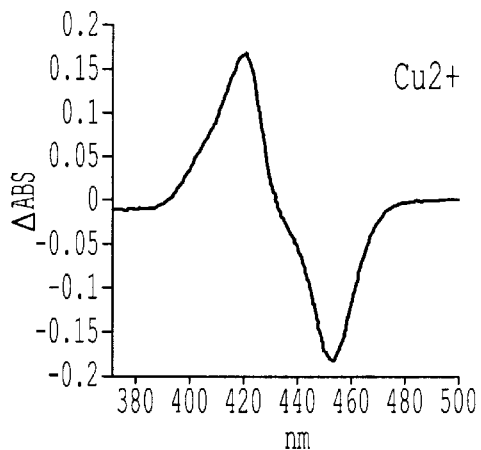
Figure 1G:
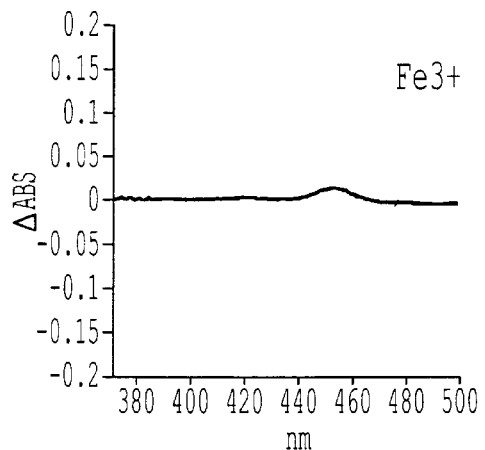
Figure 1H:
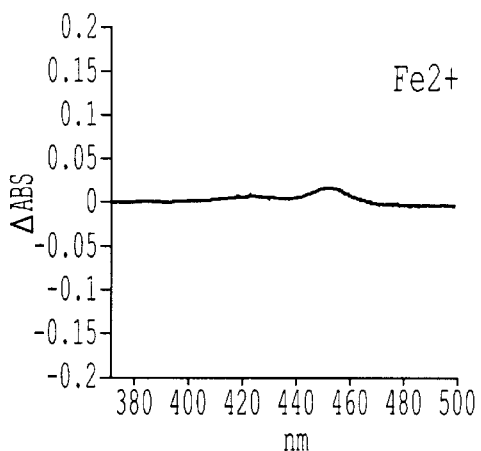
Figure 1I:
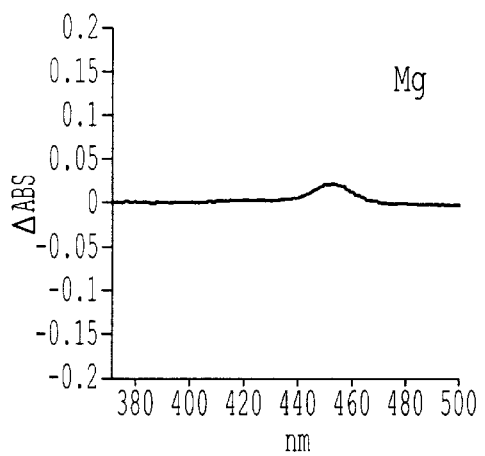
Figure 1J:
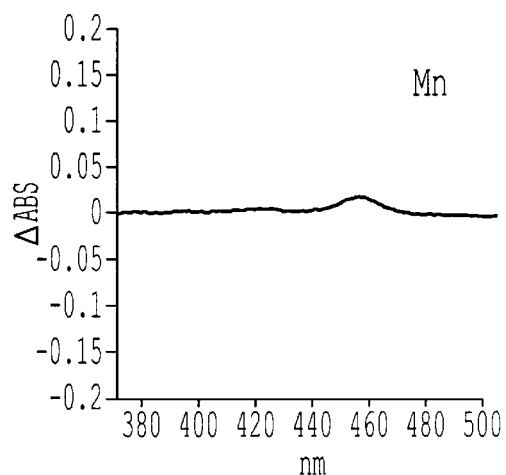
Figure 1K:
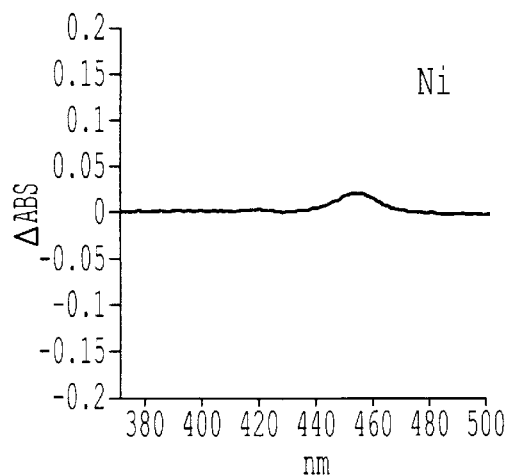
Figure 1L:
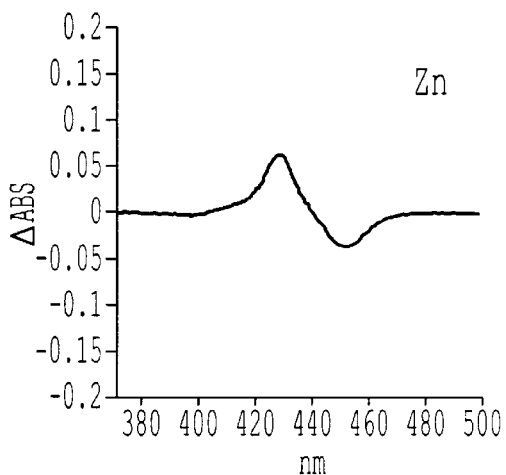
Figure 1M:
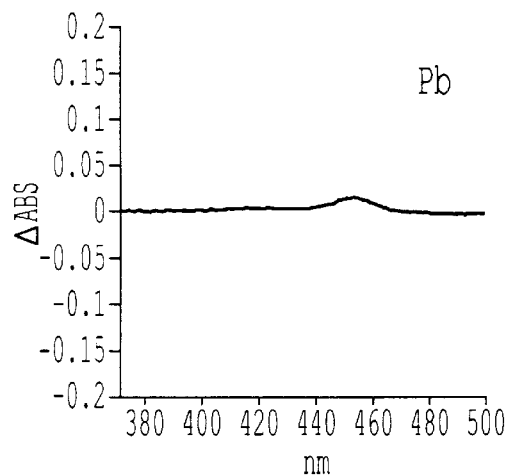
Figure 2A:
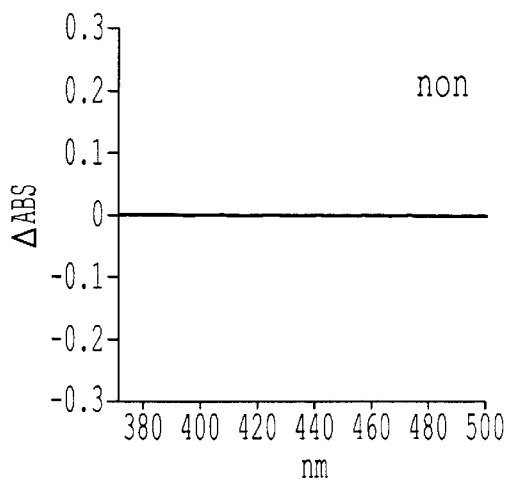
FIG. 2 illustrates a difference in the absorbance caused by the addition of a metal salt to the copolymer of TAPP and MAcid (pH 11).
Figure 2B:
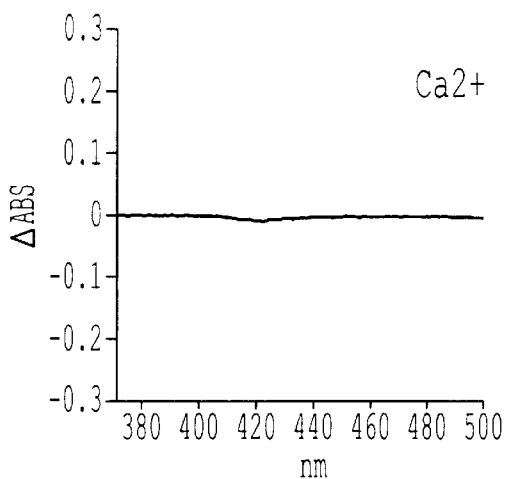
Figure 2C:
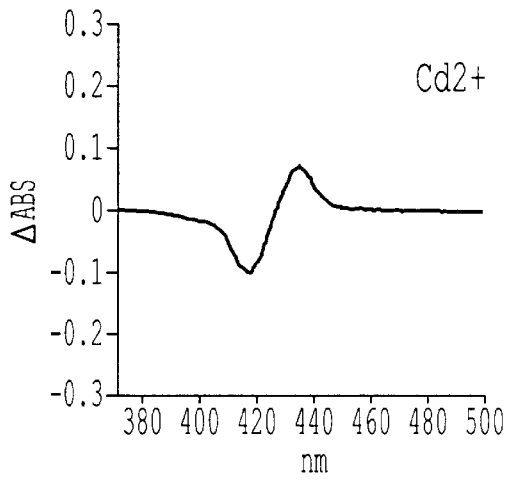
Figure 2D:
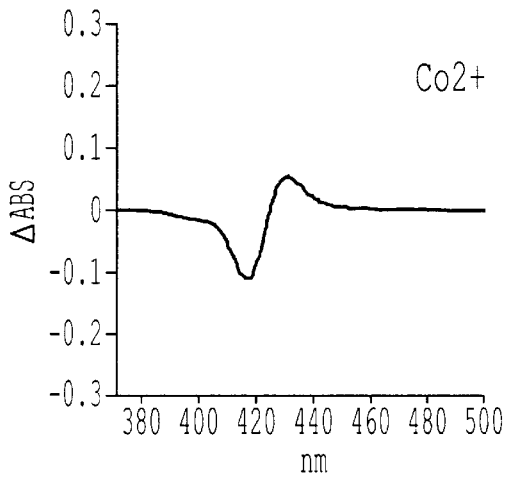
Figure 2E:
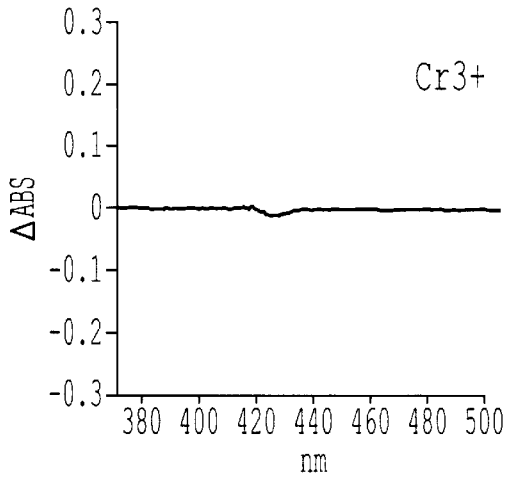
Figure 2F:
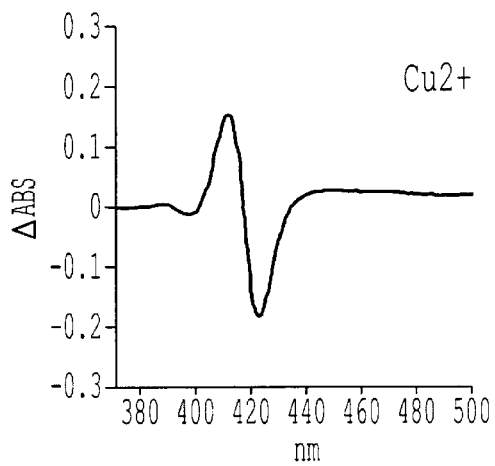
Figure 2G:
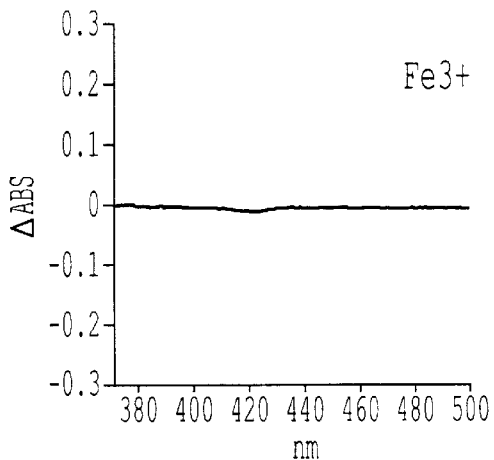
Figure 2H:
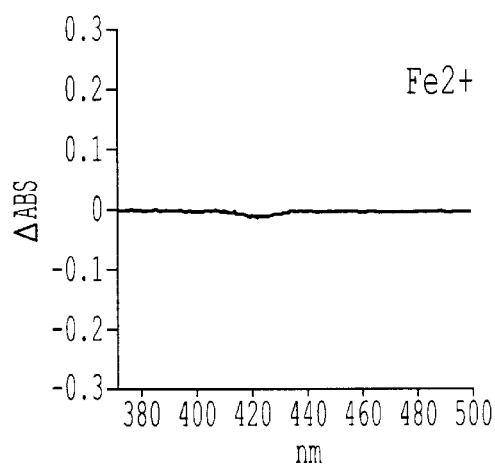
Figure 2I:
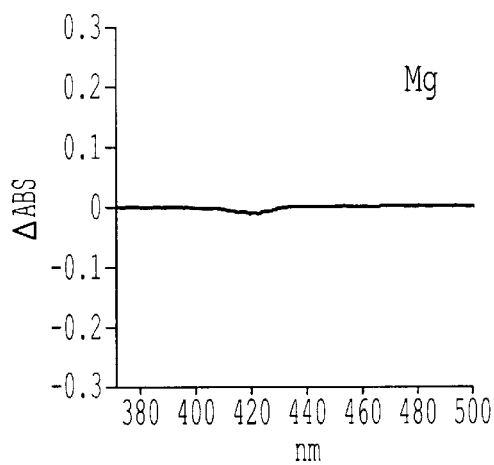
Figure 2J:
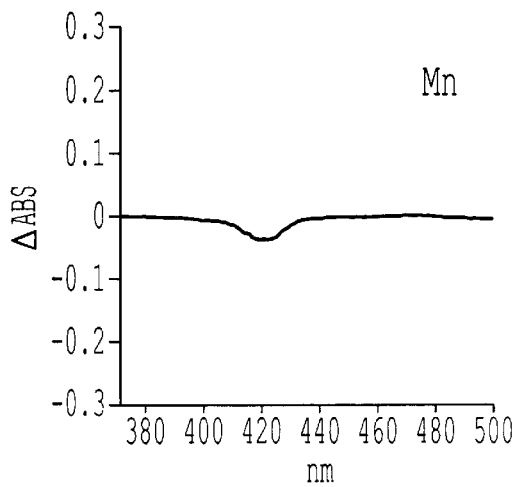
Figure 2K:
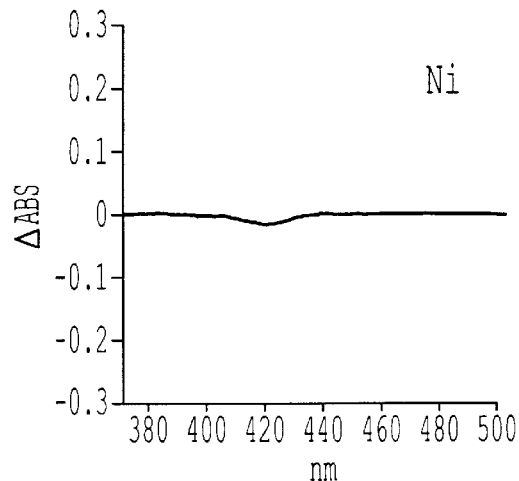
Figure 2L:
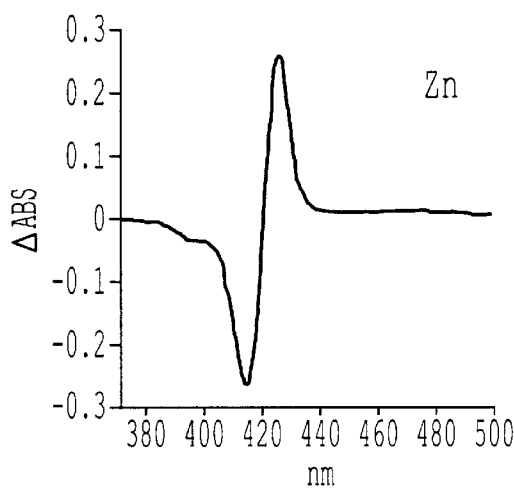
Figure 2M:
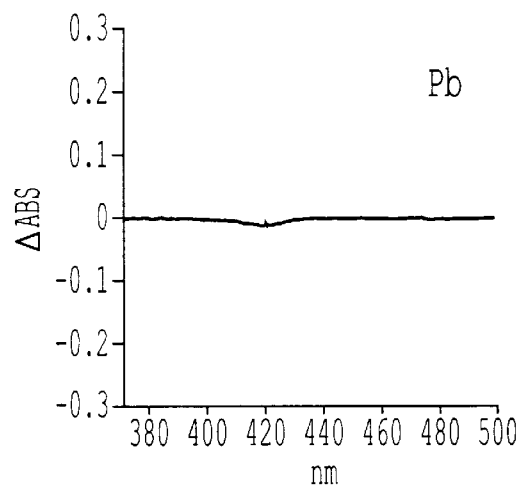
Figure 3A:
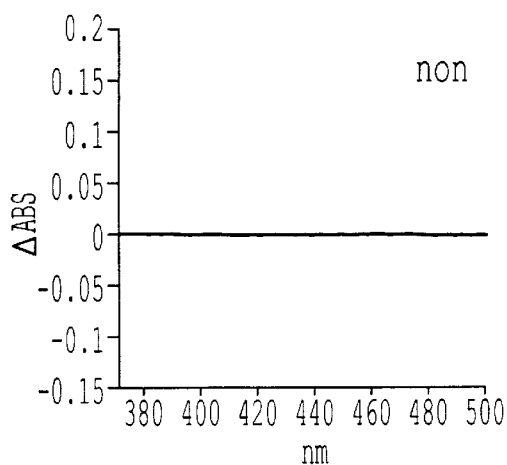
FIG. 3 illustrates a difference in the absorbance caused by the addition of a metal salt to the copolymer of protoporphyrin IX dimethyl ester (hereinafter abbreviated as "PPDE") and acrylamide (hereinafter abbreviated as "AAm") (pH 11).
Figure 3B:
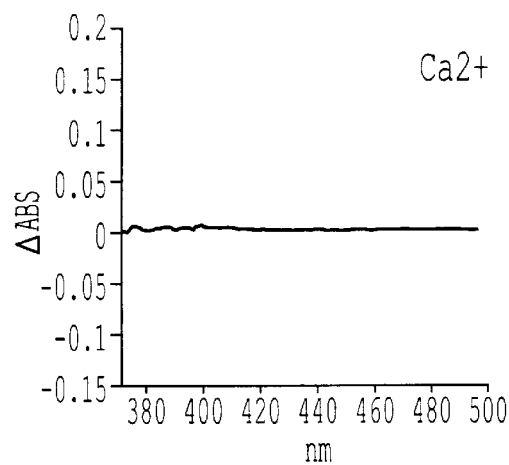
Figure 3C:
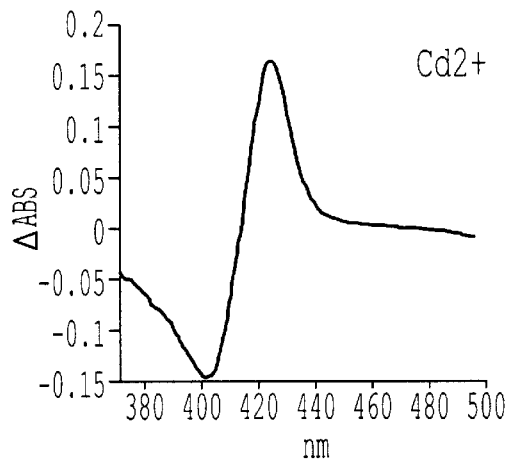
Figure 3D:
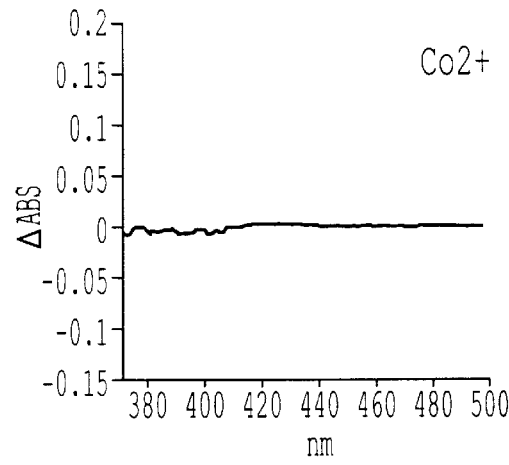
Figure 3E:
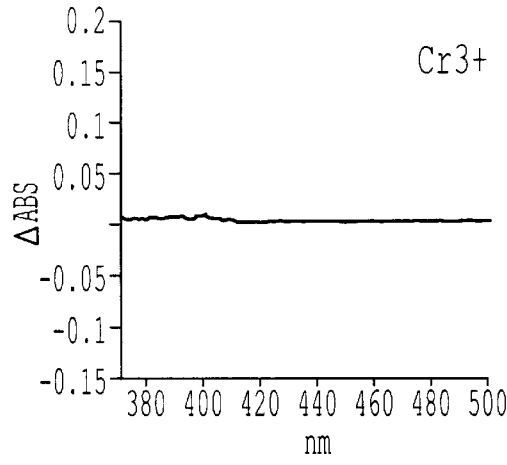
Figure 3F:
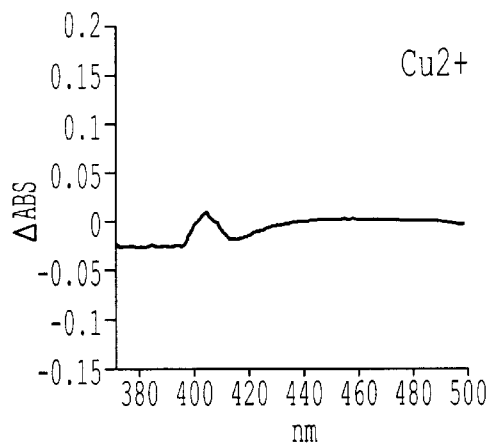
Figure 3G:
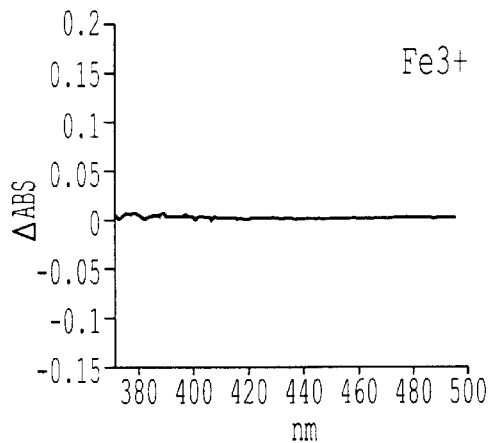
Figure 3H:
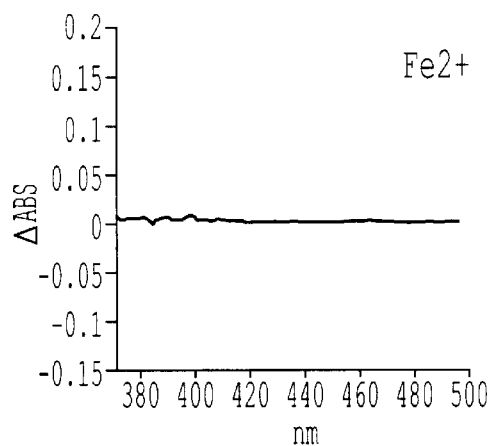
Figure 3I:
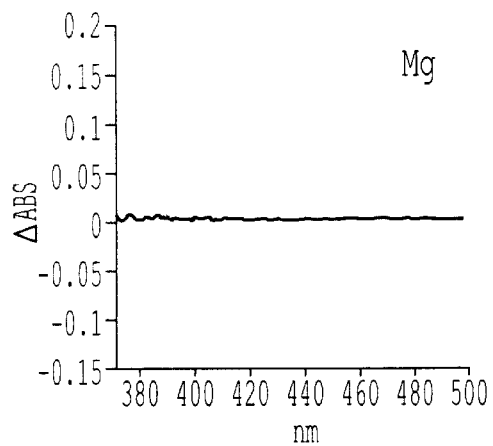
Figure 3J:
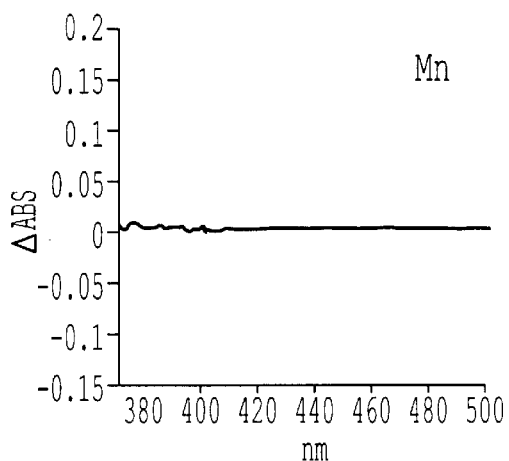
Figure 3K:
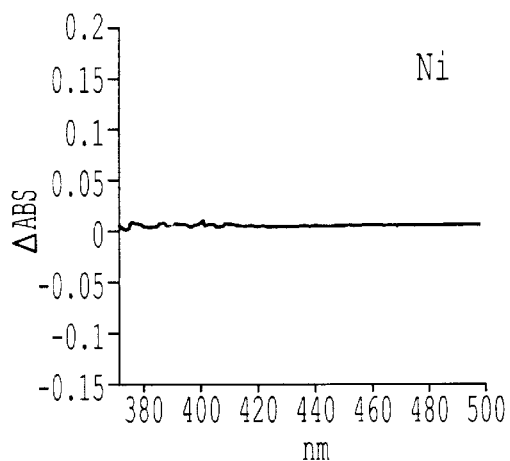
Figure 3L:
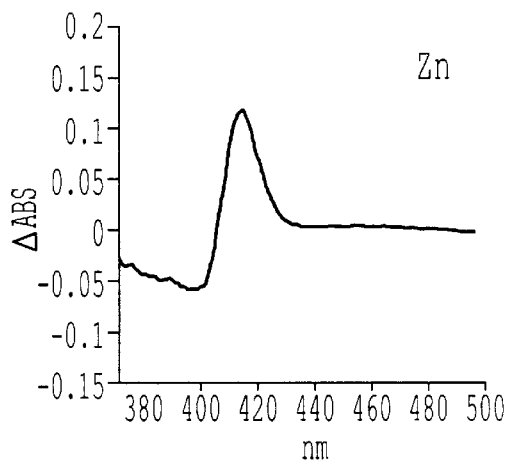
Figure 3M:
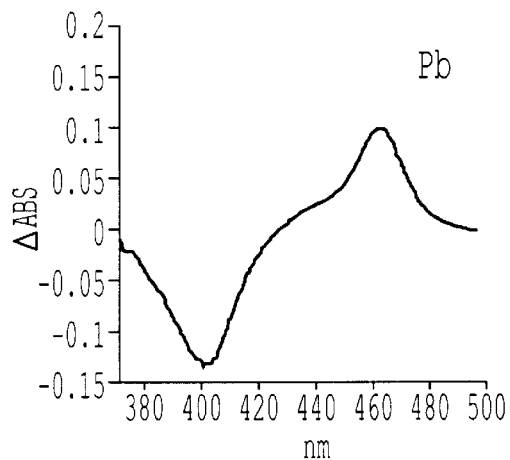
Figure 4A:
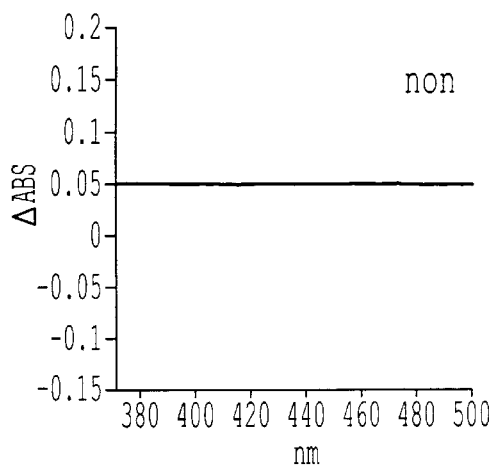
FIG. 4 illustrates a difference in the absorbance caused by the addition of a metal salt to the copolymer of PPDE and MAcid (pH 11).
Figure 4B:
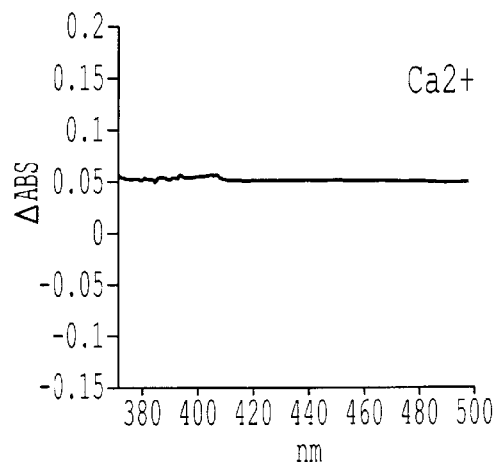
Figure 4C:
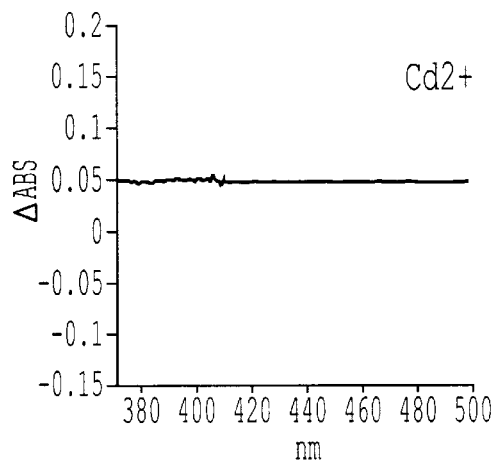
Figure 4D:
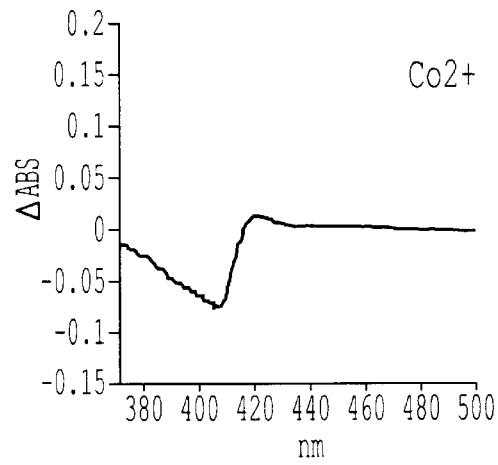
Figure 4E:
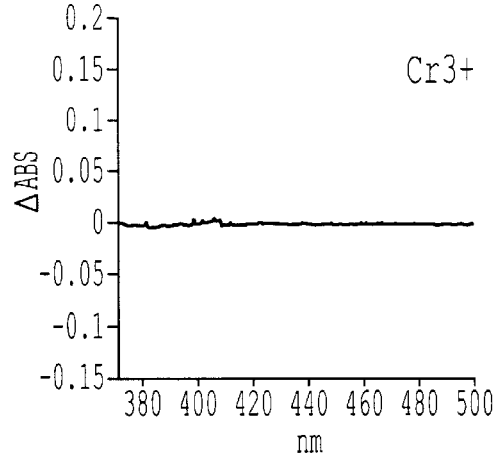
Figure 4F:
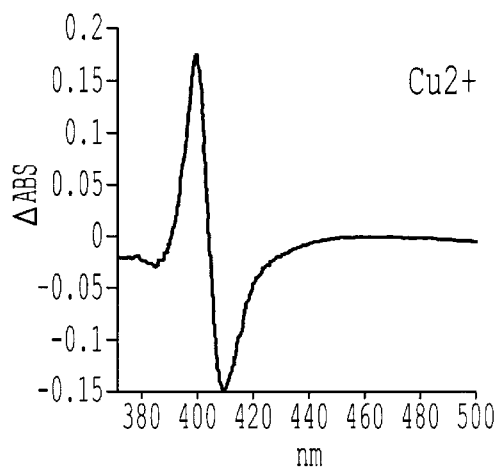
Figure 4G:
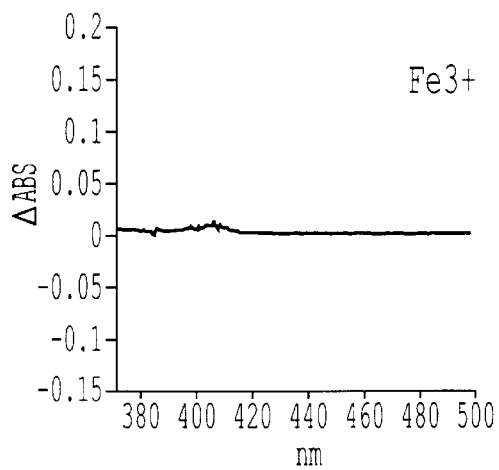
Figure 4H:
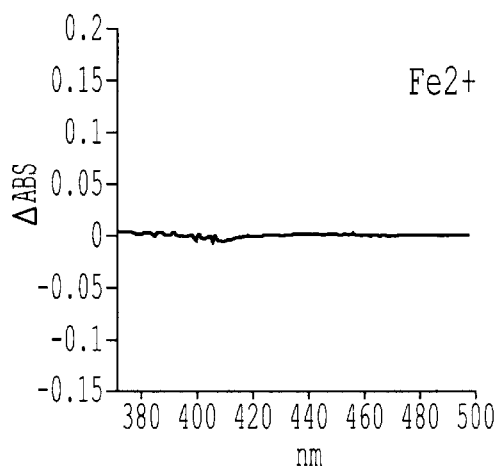
Figure 4I:
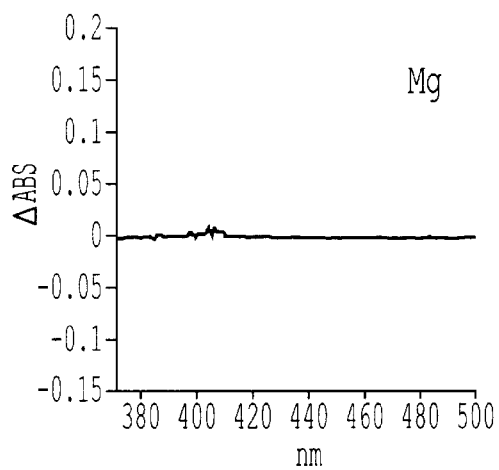
Figure 4J:
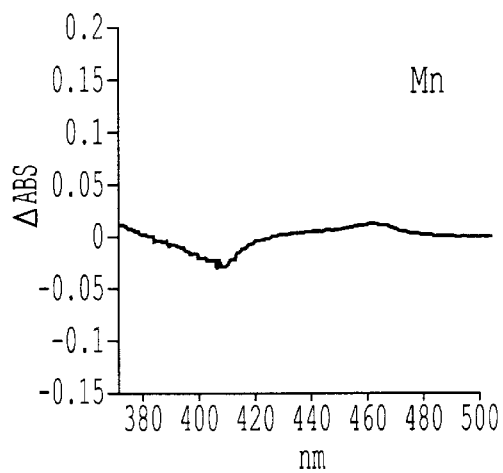
Figure 4K:
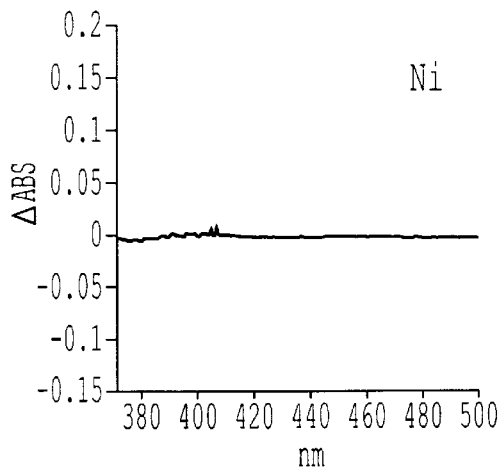
Figure 4L:
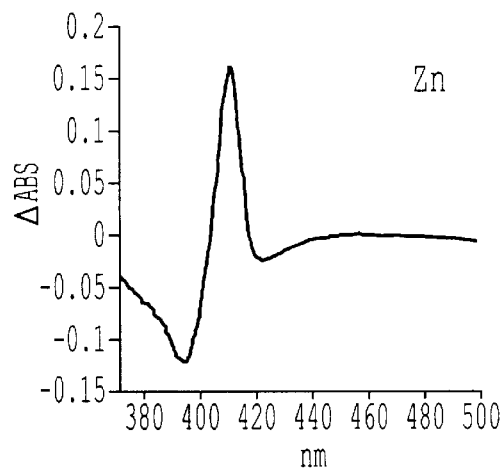
Figure 4M:
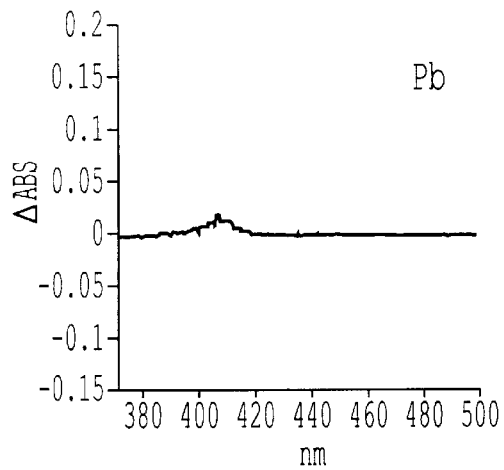

(2) Results i) Differences in the absorbance caused by the addition of metal salts at pH 5.5 or pH 11 are shown in FIGS. 1 to 4.

FIG. 1 shows a difference in the absorbance of a TAPP—methacrylic acid copolymer (TAPP-MAcid) at pH 5.5; and FIG. 2 shows a difference in the absorbance of TAPP-MAcid at pH 11. Metals causing a large absorbance difference were $Cu^{2+}$ and $Zn^{2+}$ at pH 5.5, and $Cu^{2+}$, $Zn^{2+}$, $Cd^{2+}$ and $Co^{2+}$ at pH 11.

FIG. 3 shows a difference in the absorbance of a PPDE-acrylamide copolymer (PPDE-AAm) at pH 11. A large absorbance difference was caused by $Cd^{2+}$, $Zn^{2+}$ and $Pb^{2+}$ and $Cu^{2+}$ also caused a slight absorbance difference.

FIG. 4 shows a difference in the absorbance of a PPDE—methacrylic acid copolymer (PPDE-MAcid) at pH 11. As well as a large absorbance difference caused by $Zn^{2+}$ and $Cu^{2+}$, an absorbance difference by $Co^{2+}$ and $Mn^{2+}$ which did not occur in PPDE-AAm were observed.

ii) A change in the absorbance due to complex formation between each of all the porphyrin-nucleus introduced polymers synthesized above and a metal, and wavelength are shown in Table 3. For comparison, the absorbance of a porphyrin compound itself was measured in a similar manner after dissolving it in DMSO when it was PPDE and in THF when it was TAPP, and then adjusting the pH of the resulting solution. The results are collectively shown in Table 3 (the blank column of this table indicates that a peak of difference in absorbance was not observed).

TABLE 3

| Polymer | pH | $Cd^{2+}$ | nm | $Co^{2+}$ | nm | $Cu^{2+}$ | nm | $Fe^{2+}$ | nm | $Mn^{2+}$ | nm | $Zn^{2+}$ | nm | $Pb^{2+}$ | nm |
|---|---|---|---|---|---|---|---|---|---|---|---|---|---|---|---|
| PPDE (not polymer) | 5.5 | | | | | −0.1339 | 409 | | | | | 0.024 | 413 | | |
| PPDE-AAm | 5.5 | | | | | 0.0283 | 402 | | | | | 0.0956 | 413 | | |
| PPDE-MAcid | 5.5 | | | | | 0.14 | 399 | | | | | 0.0505 | 411 | | |
| PPDE-AAcid | 5.5 | | | | | 0.1473 | 400 | | | | | 0.026 | 410 | | |
| PPDE-1VImida | 5.5 | | | | | 0.0157 | 403 | −0.025 | 471 | | | 0.0054 | 418 | | |
| PPDE-4VPyr | 5.5 | | | | | 0.1866 | 400 | | | | | 0.0341 | 402 | | |
| PPDE-5HAcid | 5.5 | | | | | 0.0326 | 399 | | | | | 0.1439 | 413 | | |
| PPDE-3BAcid | 5.5 | | | | | 0.1245 | 397 | | | | | 0.2373 | 410 | | |
| PPDE-VAce | 5.5 | | | | | | | | | | | | | | |
| PPDE-AAmine | 5.5 | | | | | 0.0421 | 395 | | | | | 0.0304 | 407 | | |
| PPDE-Achlo | 5.5 | | | | | | | | | | | | | | |
| PPDE-AA1 | 5.5 | | | | | 0.0576 | 396 | | | | | 0.0306 | 408 | | |
| PPDE-βMA1 | 5.5 | | | | | 0.1432 | 397 | | | | | 0.0221 | 410 | | |
| PPDE-DMAAm | 5.5 | | | | | 0.0709 | 401 | | | | | 0.0182 | 414 | | |
| PPfacid-AAm | 5.5 | | | 0.0199 | 425 | 0.0234 | 401 | −0.1114 | 402 | | | 0.1919 | 412 | | |
| TAPP (not polymer) | 5.5 | | | | | 0.0402 | 409 | | | | | | | | |
| TAPP-AAm | 5.5 | | | | | 0.516 | 419 | | | | | 0.0178 | 430 | | |
| TAPP-Macid | 5.5 | | | | | 0.1663 | 419 | | | | | 0.0636 | 428 | | |
| TAPP-Aacid | 5.5 | | | | | 0.3197 | 419 | | | | | | | | |
| TAPP-DMAAm | 5.5 | | | | | 0.0408 | 418 | | | | | | | | |
| PPDE (not polymer) | 11 | 0.0114 | 422 | | | 0.0456 | 399 | | | | | | | 0.0117 | 465 |
| PPDE-AAm | 11 | 0.1646 | 426 | | | −0.0188 | 415 | | | | | 0.1158 | 415 | 0.0973 | 465 |
| PPDE-MAcid | 11 | | | 0.015 | 420 | 0.1798 | 398 | | | 0.0126 | 459 | 0.1646 | 409 | | |
| PPDE-AAcid | 11 | | | | | 0.1323 | 399 | | | | | 0.0525 | 409 | | |

TABLE 3-continued

| Polymer | pH | $Cd^{2+}$ | nm | $Co^{2+}$ | nm | $Cu^{2+}$ | nm | $Fe^{2+}$ | nm | $Mn^{2+}$ | nm | $Zn^{2+}$ | nm | $Pb^{2+}$ | nm |
|---|---|---|---|---|---|---|---|---|---|---|---|---|---|---|---|
| PPDE-1VImida | 11 | 0.0334 | 426 | | | | | | | | | 0.0191 | 420 | 0.0198 | 468 |
| PPDE-4VPyr | 11 | | | | | 0.0712 | 402 | | | | | | | | |
| PPDE-5HAcid | 11 | 0.1946 | 421 | 0.0126 | 422 | | | | | 0.0276 | 458 | 0.1722 | 410 | 0.0842 | 462 |
| PPDE-3BAcid | 11 | 0.1405 | 421 | | | 0.0703 | 397 | | | 0.0111 | 458 | 0.0245 | 410 | 0.0396 | 462 |
| PPDE-VAce | 11 | | | | | | | | | | | | | | |
| PPDE-AAmine | 11 | 0.0098 | 422 | | | | | | | | | | | 0.0093 | 461 |
| PPDE-AChlo | 11 | | | | | | | | | | | | | | |
| PPDE-AA1 | 11 | 0.0071 | 420 | | | 0.0265 | 396 | | | | | | | 0.003 | 462 |
| PPDE-βMA1 | 11 | | | | | 0.076 | 397 | | | | | 0.0316 | 398 | 0.0074 | 462 |
| PPDE-DMAAm | 11 | 0.0344 | 421 | | | 0.0394 | 400 | | | | | 0.0214 | 413 | 0.0398 | 464 |
| PPfacid-AAm | 11 | 0.1611 | 426 | | | 0.0217 | 404 | | | | | 0.1002 | 415 | 0.1129 | 465 |
| TAPP (not polymer) | 11 | | | | | | | | | | | | | | |
| TAPP-AAm | 11 | 0.0944 | 442 | | | 0.0237 | 418 | | | | | 0.0534 | 436 | 0.0582 | 469 |
| TAPP-MAcid | 11 | 0.0738 | 435 | 0.0555 | 431 | 0.1339 | 411 | | | | | 0.2602 | 425 | | |
| TAPP-AAcid | 11 | | | 0.0578 | 430 | 0.3934 | 417 | | | 0.0179 | 471 | 0.3892 | 424 | | |
| TAPP-DMAAm | 11 | 0.0472 | 434 | | | 0.0359 | 419 | | | | | 0.0383 | 425 | 0.0371 | 470 |

The above-described results indicate that the kind of a metal with which the polymer reacted, difference in absorbance and absorption wavelength each differs depending on the kind of the porphyrin compound and the kind of the radically polymerizable monomer copolymerized therewith. They also indicate that by incorporation of a porphyrin nucleus in a polymer, the resulting compound forms a complex with a metal to which a porphyrin compound itself does not bind and some polymers cause a large difference in absorbance.

Example 3

Measurement of the Concentration of Heavy Metals by Using a Porphyrin-nucleus Introduced Polymer In FIG. 5, shown are reaction curves of TAPP-MAcid with $Cu^{2+}$ at pH 5.5, PPDE-AAm with $Zn^{2+}$ at pH 5.5 and PPDE-AAm with $Pb^{2+}$ at pH 11. The polymers exhibited linear reactivity with any metal. The leachate from an ash depository of a waste incinerator was used as a sample and its absorbance was measured using the above-described polymers. A metal concentration was calculated by a regression equation obtained by multiple regression analysis using standard samples. The analytical results are shown in Table 4, together with the results measured by an atomic absorption spectrophotometer. The analytical results coincided with the results of atomic absorbance spectrophotometry. The multiple correlation coefficient r in multiple regression analysis available from the standard sample used for the measurement of $Cu^{2+}$ was 0.98937 ($r^2$=0.97885), while that available from the standard sample used for the measurement of $Zn^{2+}$ was 0.97727 ($r^2$=0.95505).

TABLE 4

| | $Cu^{2+}$ | | $Zn^{2+}$ | | $Pb^{2+}$ | |
|---|---|---|---|---|---|---|
| Sample | Polymer | Atomic absorption | Polymer | Atomic absorption | Polymer | Atomic absorption |
| Leachate from ash depository | 186.3 | 174.8 | 3021 | 4917 | 38.4 | 56.4 |

Unit μM
"Polymer": absorption spectrophotometry using a porphyrin-introduced polymer
"Atomic absorption": Atomic absorption spectrometry Example 4

Synthesis of Porphyrin Nucleus-introduced Gels

Used as a porphyrin compound were PPfacid and PPDE; as a radically polymerizable monomer, four monomers, that is, acrylamide (AAm), methacrylic acid (MAcid), acrylic acid (AAcid) and N,N-dimethylacrylamide (DMAAm); and as a crosslinking agent, N,N'-methylenebisacrylamide (MBAA).

In a vessel were charged 5 ml of a 0.6 mM porphyrin solution, an adequate amount of a radically polymerizable monomer, 2 ml of 200 mM N,N'-methylenebisacrylamide and 0.2 ml of 500 mM AIBN, followed by the addition of DMSO to give the total amount of 10 ml. In consideration of the maintenance of the gel form, the radically polymerizable monomer was added so that the concentration after filling would be 1.5M.

The vessel having the reaction mixture therein was immersed in cold water filled in an ultrasonic apparatus, followed by degassing for 30 minutes. Bubbling by a nitrogen gas was then conducted for 2 minutes. The polymer solution was poured in a space of 1 mm between glass plates. The resulting plates were placed in an incubator of 60° C., whereby polymerization was initiated. After 21 hours, the gel sheet of 1 mm thick was removed from the glass plates and cut into a piece of 5 mm square. The resulting gel was washed well with pure water. In this manner, various porphyrin-nucleus introduced gels were prepared.

Example 5

Measurement of Reactivity with Metal (1) Measuring Method

To each of 5 ml a buffer solution containing 20 mM 2-(N-morpholino)ethanesulfonic acid (MES) and having a pH of 5.5 and 5 ml of a buffer solution containing 20 mM 3-cyclohexylamino-1-propanesulfonic acid (CAPS) and having a pH of 11, 50 μl of each of 500 μM aqueous solutions of metal salts shown in Table 2 was added. After the porphyrin-nucleus introduced gel sheet was immersed in the aqueous solution of a metal salt at 60° C. for 1 hour, the gel was taken out and absorbance of it (at 370 to 500 nm) in the thickness direction was measured.

Figure 6A:
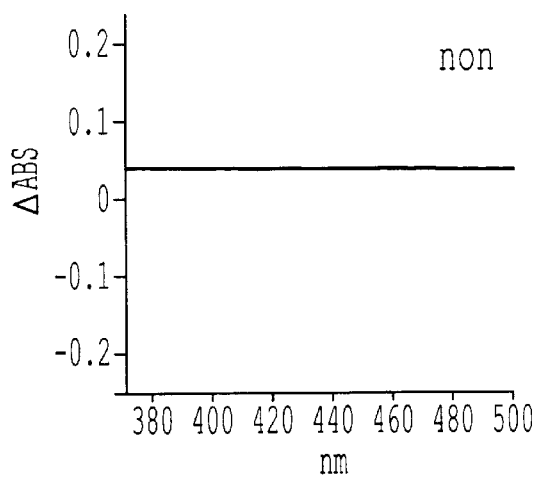
FIG. 6 illustrates a difference in the absorbance of a copolymerized gel of PPDE, acrylamide and N,N'-methylenebisacrylamide immersed in each of various aqueous metal-salt solutions (pH 11).
Figure 6B:
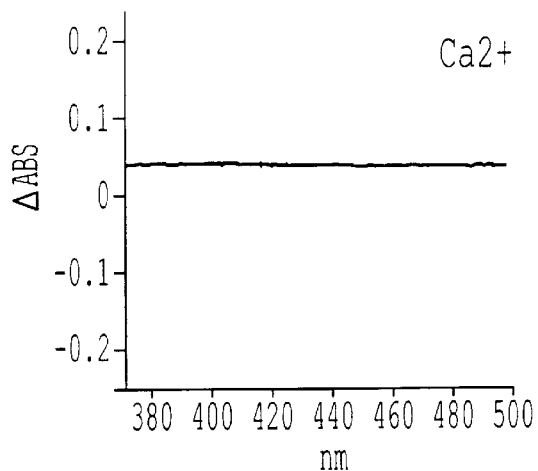
Figure 6C:
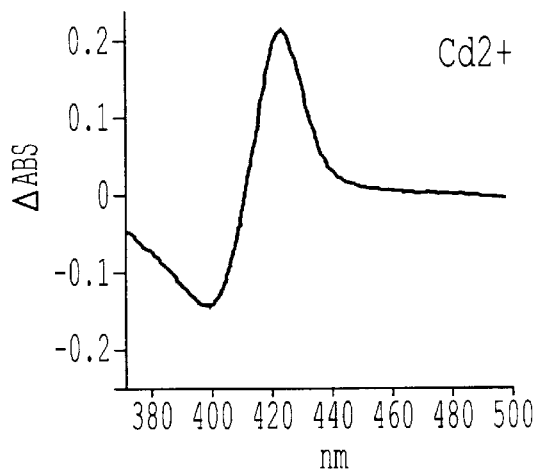
Figure 6D:
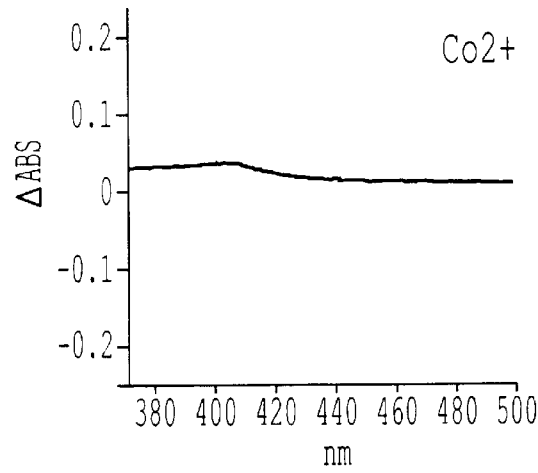
Figure 6E:
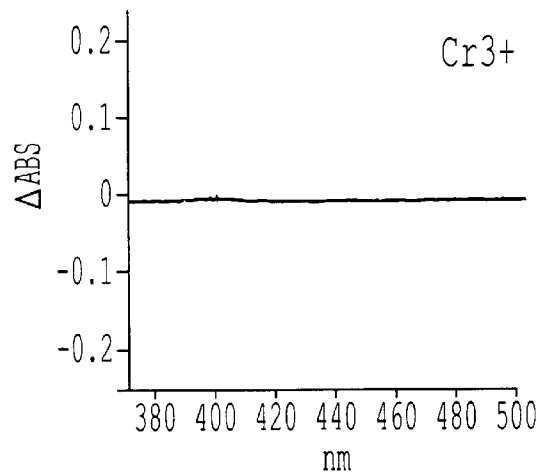
Figure 6F:
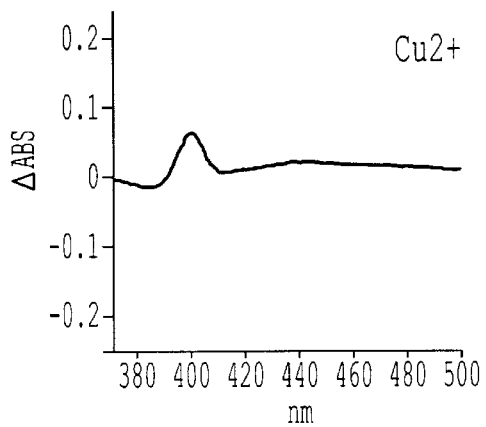
Figure 6G:
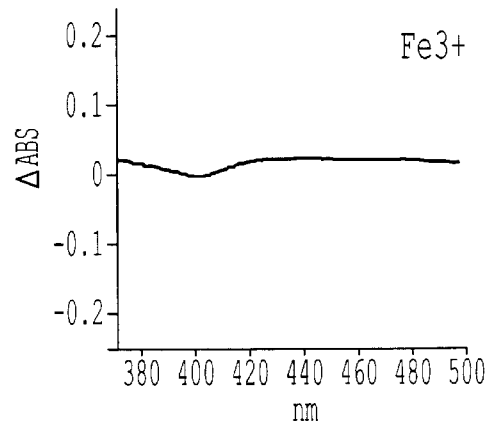
Figure 6H:
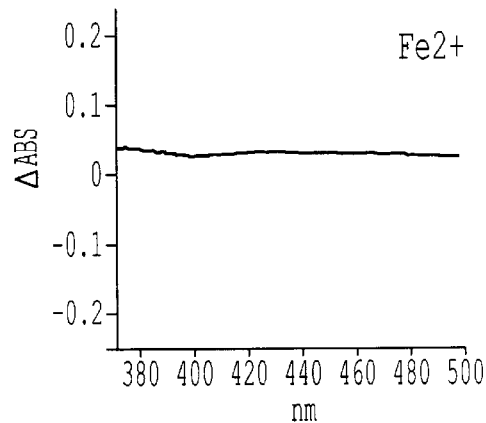
Figure 6I:
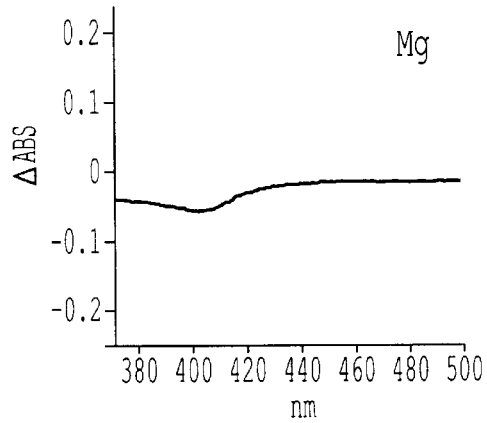
Figure 6J:
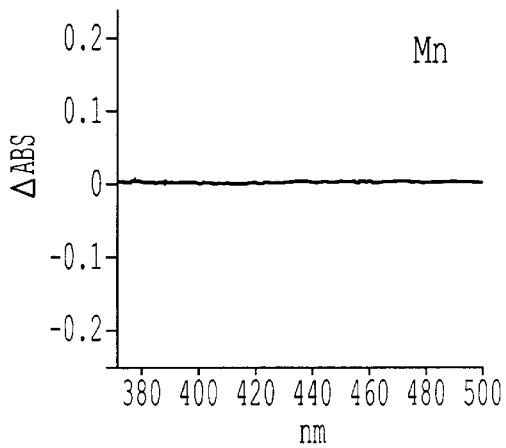
Figure 6K:
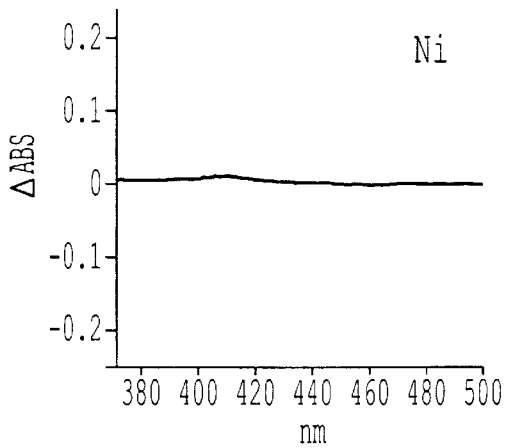
Figure 6L:
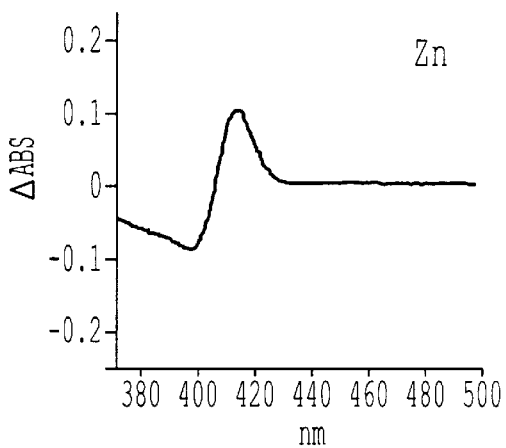
Figure 6M:
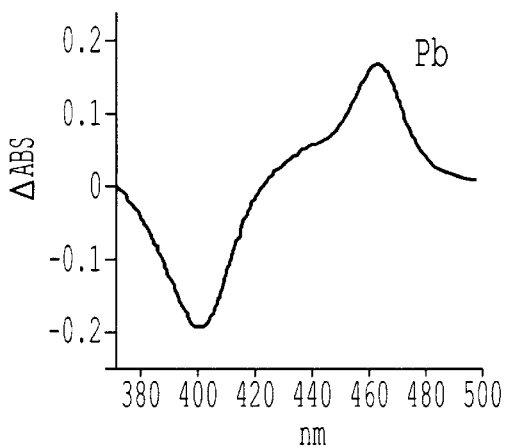

(2) Results i) Differences in the absorbance caused by immersion of the copolymerized gel of PPDE, acrylamide and N,N'-methylenebisacrylamide in aqueous solutions of metal salts haring a pH 11 are shown in FIG. 6. Metals causing a large absorbance difference were $Cu^{2+}$, $Zn^{2+}$, $Cd^{2+}$ and $Pb^{2+}$.

ii) A change in the absorbance due to complex formation between each of all the porphyrin-nucleus introduced gels synthesized above and a metal, and wavelength are shown in Table 5. For comparison, the absorbance of PPDE itself was measured in a similar manner after dissolving it in DMSO, and then adjusting the pH of the resulting solution. The results are collectively shown in Table 5 (the blank column of this table indicates that a peak of difference in absorbance was not observed).

TABLE 5

| Gel | pH | $Cd^{2+}$ | nm | $Cu^{2+}$ | nm | $Zn^{2+}$ | nm | $Pb^{2+}$ | nm |
|---|---|---|---|---|---|---|---|---|---|
| PPDE (not gel) | 5.5 | | | −0.0627 | 399 | 0.024 | 413 | | |
| PPDE-AAm-MBAA | 5.5 | | | 0.0611 | 399 | 0.0616 | 412 | | |
| PPDE-MAcid-MBAA | 5.5 | | | 0.2231 | 398 | −0.0277 | 415 | | |
| PPDE-AAcid-MBAA | 5.5 | | | 0.0512 | 399 | 0.0148 | 410 | | |
| PPDE-DMAAm-MBAA | 5.5 | | | 0.0326 | 399 | | | | |
| PPfacid-AAm-MBAA | 5.5 | | | 0.0345 | 399 | 0.0824 | 411 | | |
| PPDE-(not gel) | 11 | 0.0114 | 422 | 0.0456 | 399 | | | 0.0117 | 465 |
| PPDE-AAm-MBAA | 11 | 0.2126 | 424 | 0.0629 | 400 | 0.0993 | 413 | 0.1614 | 464 |
| PPDE-MAcid-MBAA | 11 | | | −0.0237 | 395 | | | | |
| PPDE-AAcid-MBAA | 11 | | | −0.0243 | 398 | | | | |
| PPDE-DMAAm-MBAA | 11 | 0.0346 | 423 | 0.0276 | 399 | | | 0.0364 | 464 |
| PPfacid-AAm-MBAA | 11 | 0.1158 | 423 | 0.042 | 400 | 0.0687 | 413 | 0.1105 | 464 |

While the present invention has been described with respect to specific embodiments, it is not confined to the specific details set forth, but includes various changes and modifications that may suggest themselves to those skilled in the art, all falling with the scope of the invention as defined by the following claims.

What is claimed is:

1. A method of controlling reactivity of a porphyrin-nucleus introduced polymer with a metal, the method comprising
   selecting a radically polymerizable monomer; and
   copolymerizing the radically polymerizable monomer and a vinyl-containing porphyrin compound to obtain the porphyrin-nucleus introduced polymer, wherein
   the vinyl-containing porphyrin compound is represented by any one of the following formulas (1) to (2):

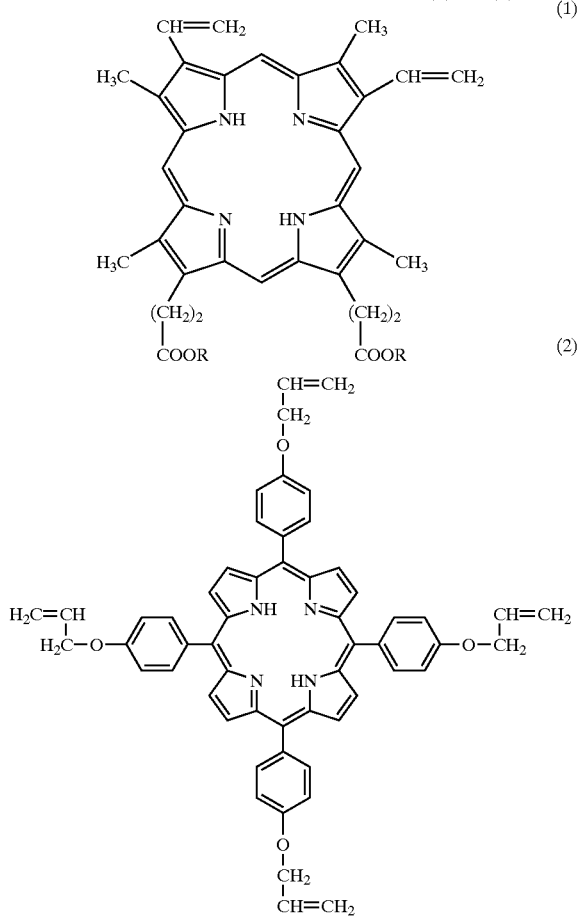

where R represents a hydrogen atom or a $C_{1-6}$ alkyl group.

2. The method according to claim 1, wherein the radically polymerizable monomer is represented by the following formula (6):

where $R^1$, $R^2$, $R^3$ and $R^4$ each independently represents
   a hydrogen atom;
   a $C_{1-5}$ alkyl group;
   —$(CH_2)_nCOOR^5$, —$(CH_2)_nOCOR^5$, —$(CH_2)_nN(R^5)(R^6)$, —$(CH_2)_nCON(R^5)(R^6)$, or —$(CH_2)_nA$ in which $R^5$ and $R^6$ each represents a hydrogen atom, a $C_{1-5}$ alkyl group, a carboxymethyl group, or a phenyl or phenylalkyl group which may have a substituent, A represents a halogen atom, a hydroxyl group, a formyl group, a cyano group or a carbonyl halide group, and n stands for an integer of 0 to 6; or
   an imidazolyl, pyridyl or phenyl group which may have a substituent.

3. The method according to claim 1, wherein the radically polymerizable monomer is selected from the group consisting of acrylamide, methacrylic acid, acrylic acid, 5-hexenoic acid, allylamine, 3-butenoic acid, β-methallyl alcohol, allyl alcohol, N,N-dimethylacrylamide, 1-vinylimidazole, 2-vinylpyridine, 4-vinylpyridine, allyl chloride, vinyl acetate, maleamide, maleic acid, dimethyl maleate, diethyl maleate, maleinamic acid, methyl hydrogen maleate, ethyl hydrogen maleate, fumaramide, fumaric acid, dimethyl fumarate, diethyl fumarate, ethyl hydrogen fumarate, fumaronitrile, fumaryl chloride, crotonamide, crotonic acid, crotonaldehyde, methyl crotonate, ethyl crotonate, crotononitrile, crotonoyl bromide, crotonoyl chloride, crotyl alcohol, crotyl bromide, crotyl chloride, isocrotonic acid, trans-1,2-dichloroethylene, citraconic acid, dimethyl citraconate, mesaconic acid, angelic acid, methyl angelate, tiglic acid, methyl tiglate, ethyl tiglate, tigloyl chloride, tiglic aldehyde, N-tigloylglycine, cinnamaldehyde, cinnamamide, cinnamic acid, ethyl cinnamate, methyl cinnamate, cinnamonitrile, cinnamoyl chloride, cinnamyl bromide, cinnamyl chloride, 3-methyl-2-butenal, 2-methyl-2-butene, 2-methyl-2-butenenitrile, 3-methyl-2-buten-1-ol, and cis-1,2-dichloroethylene.

4. A method of controlling reactivity of a porphyrin-nucleus introduced polmer with a metal, the method comprising
   selecting a radically polymerizable monomer; and
   copolymerizing the radically polymerizable monomer and a vinyl-containing porphyrin compound to obtain the porphyrin-nucleus introduced polymer, wherein the radically polymerizable monomer consists of a compound represented by the following formula (6):

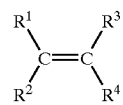

(6)

where $R^1$, $R^2$, $R^3$ and $R^4$ each independently represents
a hydrogen atom;
a $C_{1-5}$ alkyl group;
$-(CH_2)_nCOOR^5$, $-(CH_2)_nOCOR^5$, $-(CH_2)_nN(R^5)(R^6)$, $-(CH_2)_nCON(R^5)(R^6)$, or $-(CH_2)_nA$ in which $R^5$ and $R^6$ each represents a hydrogen atom, a $C_{1-5}$ alkyl group, a carboxymethyl group, or a phenyl or phenylalky1 group which may have a substituent, A represents a halogen atom, a hydroxyl group, a formnyl group, a cyano group or a carbonyl halide group, and n stands for an integer of 0 to 6; or
an imidazolyl, pyridyl or phenyl group which may have a substituent; and
a compound having at least two polymerizable carbon-carbon double bonds; and
the method further comprises crosslinking the porphyrin-nucleus introduced polymer using the radically polymerizable monomer.

5. The method according to claim 4, wherein the compound having at least two polymerizable carbon-carbon double bonds is selected from the group consisting of N-N'-methylene-bis(acrylamide), ethylene glycol diacrylate; N,N'-bis(acrylolyl)cystamine; divinylbenzene; tetramethylolmethane tetraacrylate; and trimethylolpropane triacrylate.

6. The method according to claim 1, wherein the copolymerizing is carried out at a temperature within a range of from 55° C. to 65° C.

7. A trace metal detection method, the method comprising
selecting a radically polymerizable monomer;
copolymerizing the radically polymerizable monomer and a vinyl-containing porphyrin compound to obtain a porphyrin-nucleus introduced polymer;
reacting the porphyrin-nucleus introduced polymer with a trace metal contained in a sample to form a reaction mixture;
measuring a change in light absorbance of the reaction mixture resulting from the reaction of the porphyrin-nucleus introduced polymer and the trace metal; and
determining a concentration of the trace metal in the sample.

8. The method according to claim 7, further comprising adding the porphyrin-nucleus introduced polymer to a buffer solution before the porphyrin-nucleus introduced polymer is reacted with the trace metal.

9. The method according to claim 7, wherein the trace metal is a metal ion selected from the group consisting of $Ca^{2+}$, $Cd^+$, $Co^{2+}$, $Cr^{3+}$, $Cu^{2+}$, $Fe^{3+}$, $Fe^{2+}$, $Mg^{2+}$, $Mn^{2+}$, $Ni^{2+}$, $Zn^{2+}$ and $Pb^{2+}$.

10. The method according to claim 7, wherein as the vinyl-containing porphyrin compound is represented by any one of the following formulas (1) to (5):

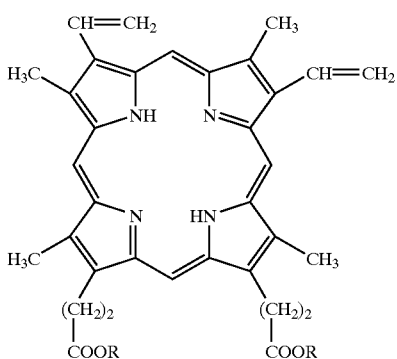

(1)

-continued
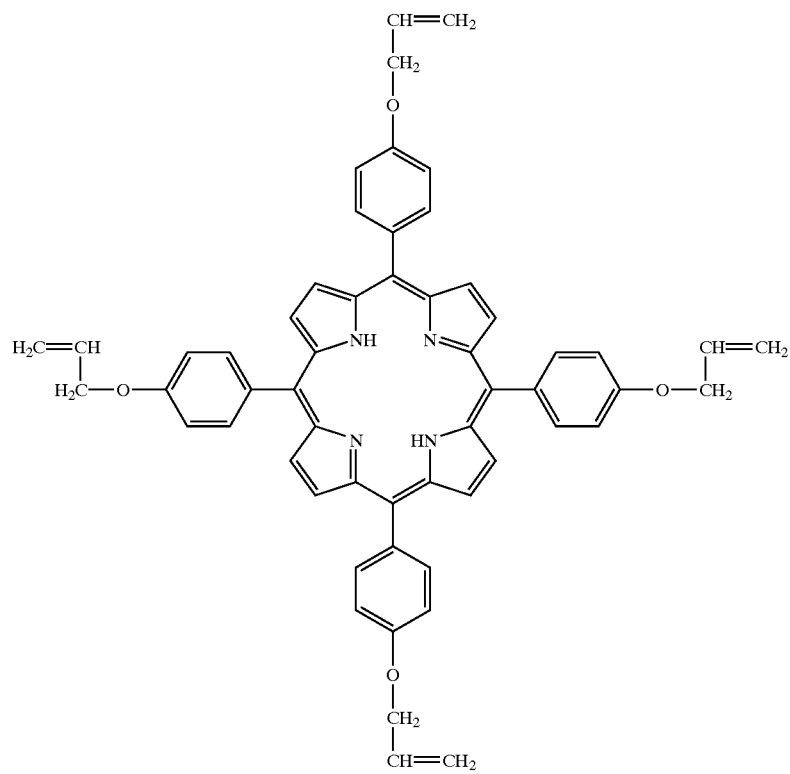
(2)
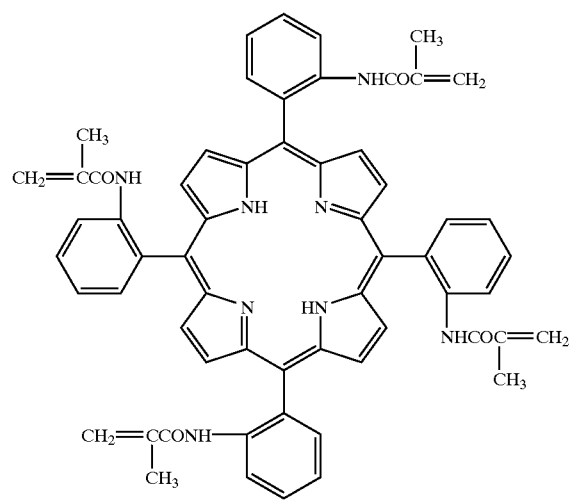
(3)
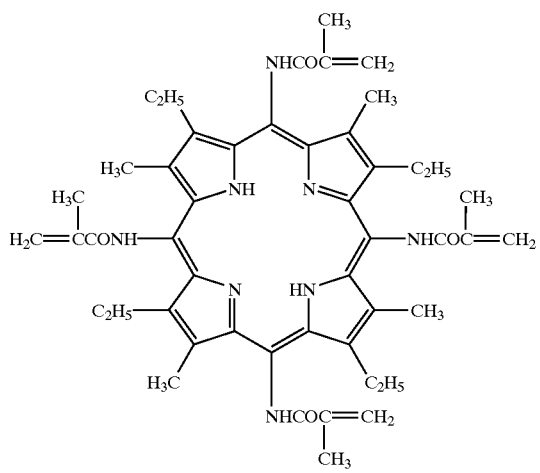
(4)

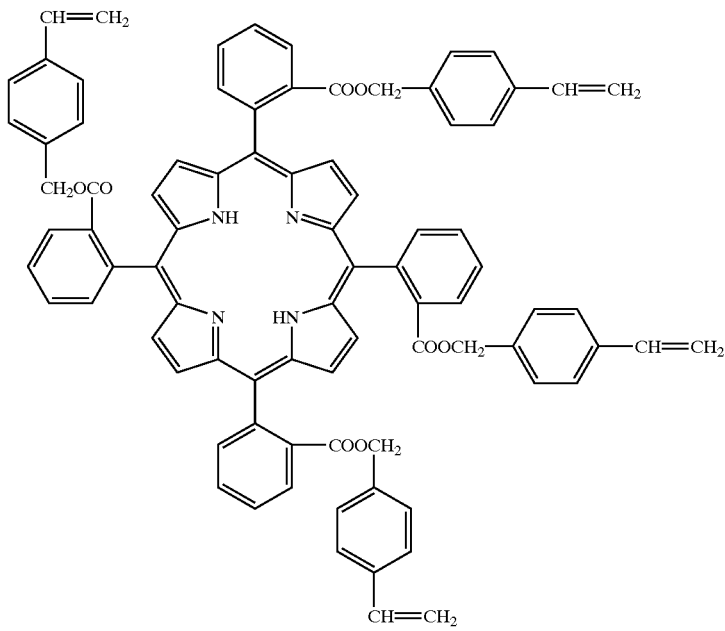
(5)

where R represents a hydrogen atom or a $C_{1-6}$ alkyl group.

11. A trace metal measuring method according to claim 7, wherein as the radically polymerizable monomer, used is a compound represented by the following formula (6):

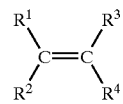
(6)

where $R^1$, $R^2$, $R^3$ and $R^4$ each independently represents
a hydrogen atom;
a $C_{1-5}$ alkyl group;
—$(CH_2)_n COOR^5$, —$(CH_2)_n OCOR^5$, —$(CH_2)_n N(R^5)(R^6)$, —$(CH_2)_n CON(R^5)(R^6)$, or —$(CH_2)_n A$ in which $R^5$ and $R^6$ each represents a hydrogen atom, a $C_{1-5}$ alkyl group, a carboxymethyl group, or a phenyl or phenylalkyl group which may have a substituent, A represents a halogen atom, a hydroxyl group, a formyl group, a cyano group or a carbonyl halide group, and n stands for an integer of 0 to 6; or
an imidazolyl, pyridyl or phenyl group which may have a substituent.

12. The method according to claim 7, wherein the radically polymerizable monomer is selected from the group consisting of acrylamide, methacrylic acid, acrylic acid, 5-hexenoic acid, allylamine, 3-butenoic acid, β-methallyl alcohol, allyl alcohol, N,N-dimethylacrylamide, 1-vinylimidazole, 2-vinylpyridine, 4-vinylpyridine, allyl chloride, vinyl acetate, maleamide, maleic acid, dimethyl maleate, diethyl maleate, maleinamic acid, methyl hydrogen maleate, ethyl hydrogen maleate, fumaramide, fumaric acid, dimethyl fumarate, diethyl fumarate, ethyl hydrogen fumarate, fumaronitrile, fumaryl chloride, crotonamide, crotonic acid, crotonaldehyde, methyl crotonate, ethyl crotonate, crotononitrile, crotonoyl bromide, crotonoyl chloride, crotyl alcohol, crotyl bromide, crotyl chloride, isocrotonic acid, trans-1,2-dichloroethylene, citraconic acid, dimethyl citraconate, mesaconic acid, angelic acid, methyl angelate, tiglic acid, methyl tiglate, ethyl tiglate, tigloyl chloride, tiglic aldehyde, N-tigloylglycine, cinnamaldehyde, cinnamamide, cinnamic acid, ethyl cinnamate, methyl cinnamate, cinnamonitrile, cinnamoyl chloride, cinnamyl bromide, cinnamyl chloride, 3-methyl-2-butenal, 2-methyl-2-butene, 2-methyl-2-butenenitrile, 3-methyl-2-buten-1-ol, and cis-1,2-dichloroethylene.

13. The method according to claim 7, wherein the radically polymerizable monomer consists of
a compound represented by the following formula (6):

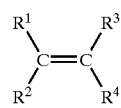
(6)

where $R^1$, $R^2$, $R^3$ and $R^4$ each independently represents
a hydrogen atom;
a $C_{1-5}$ alkyl group;
—$(CH_2)_n COOR^5$, —$(CH_2)_n OCOR^5$, —$(CH_2)_n N(R^5)(R^6)$, —$(CH_2)_n CON(R^5)(R^6)$, or —$(CH_2)_n A$ in which $R^5$ and $R^6$ each represents a hydrogen atom, a $C_{1-5}$ alkyl group, a carboxymethyl group, or a phenyl or phenylalkyl group which may have a substituent, A represents a halogen atom, a hydroxyl group, a formyl group, a cyano group or a carbonyl halide group, and n stands for an integer of 0 to 6; or an imidazolyl, pyridyl or phenyl group which may have a substituent; and a compound having at least two polymerizable carbon-carbon double bonds; and the method further comprises crosslinking the porphyrin-nucleus introduced polymer using the radically polymerizable monomer.

14. The method according to claim 13, wherein the compound having at least two polymerizable carbon-carbon double bonds is selected from the group consisting of N-N'-methylene-bis(acrylamide), ethylene glycol diacrylate; N,N'-bis(acrylolyl)cystamine; divinylbenzene; tetramethylolmethane tetraacrylate; and trimethylolpropane triacrylate.

15. The method according to claim 7, wherein plural trace metals are measured simultaneously by using plural porphyrin-nucleus introduced polymers in combination.

16. The method according to claim 4, wherein the copolymerizing is carried out at a temperature within a range of from 55° C. to 65° C.

* * * * *

UNITED STATES PATENT AND TRADEMARK OFFICE
CERTIFICATE OF CORRECTION

PATENT NO. : 6,515,089 B1
DATED : February 4, 2003
INVENTOR(S) : Takaharu Asano et al.

It is certified that error appears in the above-identified patent and that said Letters Patent is hereby corrected as shown below:

Column 17,
Line 15, "$(CH_2)_nCOOR^5$" should read -- —$(CH_2)_nCOOR^5$ --.
Line 21, "formnyl" should read -- formyl --.

Column 18,
Line 31, "$Cd^+$" should read -- $Cd^{2+}$ --.

Column 21,
Line 46, "—$CH_2)_nOCOR^5$" should read -- —$(CH_2)_nOCOR^5$ --.

Signed and Sealed this

Twenty-fourth Day of June, 2003

JAMES E. ROGAN
*Director of the United States Patent and Trademark Office*